(12) United States Patent
Eriksson et al.

(10) Patent No.: US 10,543,270 B2
(45) Date of Patent: *Jan. 28, 2020

(54) METHODS OF TREATING WOUNDS IN A DIABETIC SUBJECT

(71) Applicants: CSL LIMITED, Parkville, Victoria (AU); B-CREATIVE SWEDEN AB, Balsta (SE)

(72) Inventors: Ulf Eriksson, Stockholm (SE); Annelie Falkevall, Stockholm (SE); Annika Mehlem, Stockholm (SE)

(73) Assignees: CSL LIMITED, Parkville, Victoria (AU); B-CREATIVE SWEDEN AB, Balsta (SE)

( * ) Notice: Subject to any disclaimer, the term of this patent is extended or adjusted under 35 U.S.C. 154(b) by 32 days.

This patent is subject to a terminal disclaimer.

(21) Appl. No.: 15/105,732

(22) PCT Filed: Dec. 18, 2014

(86) PCT No.: PCT/AU2014/050431
§ 371 (c)(1),
(2) Date: Jun. 17, 2016

(87) PCT Pub. No.: WO2015/089585
PCT Pub. Date: Jun. 25, 2015

(65) Prior Publication Data
US 2016/0319008 A1 Nov. 3, 2016

(30) Foreign Application Priority Data

Dec. 18, 2013 (AU) .................... 2013904942
Dec. 19, 2013 (AU) .................... 2013904966

(51) Int. Cl.
*A61K 39/395* (2006.01)
*C07K 16/22* (2006.01)

(52) U.S. Cl.
CPC .......... *A61K 39/3955* (2013.01); *C07K 16/22* (2013.01); *C07K 2317/24* (2013.01); *C07K 2317/56* (2013.01); *C07K 2317/565* (2013.01); *C07K 2317/76* (2013.01); *C07K 2318/00* (2013.01)

(58) Field of Classification Search
None
See application file for complete search history.

(56) References Cited

U.S. PATENT DOCUMENTS

| | | | |
|---|---|---|---|
| 7,341,996 B2 * | 3/2008 | Eriksson | C07K 14/52 514/13.3 |
| 9,139,664 B2 * | 9/2015 | Finkielsztein | A61L 26/0066 |
| 9,259,507 B2 * | 2/2016 | Simonton | A61L 26/0066 |
| 2004/0005671 A1 | 1/2004 | Nash et al. | |

FOREIGN PATENT DOCUMENTS

| | | |
|---|---|---|
| JP | 2008-508325 A | 3/2008 |
| WO | WO 03/063904 A2 | 8/2003 |
| WO | WO 2005/087812 A1 | 9/2005 |
| WO | 2006012688 A1 | 2/2006 |
| WO | WO 2007/140534 A1 | 12/2007 |
| WO | WO 2009/045356 A2 | 4/2009 |
| WO | WO 2009/126698 A2 | 10/2009 |

OTHER PUBLICATIONS

Brem et al. J. Clin. Invest. 117(5): 1219-1222, 2007.*
Frank et al. J. Biol. Chem. 270(21): 12607-12613, 1995.*
Zhou et al. Med Hypotheses (2015) (http://dx.doi.org/10.1016/j.mehy.2015.06.017).*
Margolis et al. Diabetes Care 31:1331-1336, 2008.*
"Diabetic nephropathy"; Mayo Clinic downloaded Apr. 15, 2019 (https://www.mayoclinic.org/diseases-conditions/diabetic-nephropathy/symptoms-causes/syc-20354556?p=1).*
European Examination Search Report dated Jul. 17, 2017 issued in corresponding European Patent Application No. 14871427.2.
Sands, Michelle, et al., "Placenta Growth Factor and Vascular Endothelial Growth Factor B Expression in the Hypoxic Lung"; Respiratory Research 2011, 12:17; pp. 1-13.
Berdel and Jenssen;"No Association between Glycemia and Wound Healing in an Experimental db/db Mouse Model"; ISRN Endicrinology, vol. 2013, Article ID 307925, Sep. 2013.
Li, Xuri, et al.; "Arteriosclerosis, Thrombosis, and Vascular Biology" Arterioscler Thromb Vasc Biol. 2008;28:1614-1620, May 29, 2008; American Heart Association.
Li, Xuri, et al.; "Reevaluation of the Role of VEGF-B Suggests a Restricted Role in the Revascularization of the Ischemic Myocardium"; Arterioscler Thromb Vasc Biol. 2008:28:1614-1620; May 21, 2008.
Schroeder, Harry W. Jr.; "Structure and Function of Immunoglobins"; J. Allergy Clin Immunol. Feb. 2010; 125 (202) S41-S52.
International Search Report and Written Opinion dated Mar. 5, 2015 issued in PCT/AU2014/050431.
Hagberg, Carolina E., "Targeting VEGF-B as a novel treatment for insulin resistance and type 2 diabetes" Nature (Oct. 18, 2012), vol. 490, pp. 426-432.
Li, Xuri et al., "Complicated life, complicated VEGF-B", Trends in Molecular Medicine (Feb. 2012), vol. 18, No. 2, pp. 119-127.
Holcomb V.B. et al., "Obesity Impairs Wound Healing in Ovariectomized Female Mice", In Vivo 23:515-518 (2009).
Pierpont Y.N. et al., "Obesity and Surgical Wound Healing: A Current Review", Hindawi Publishing Corporation, vol. 2014, Article ID 638936, 13 pages (2014).
Takeda E. et al., "An Experimental Study on Wound-Healing Process and Influence of Insulin in the Streptozotocin-Induced Diabetic Rates", Journal of Tokyo Dental College Society 102(11):885-904 (2002), together with an English-language abstract.

(Continued)

*Primary Examiner* — Christine J Saoud
(74) *Attorney, Agent, or Firm* — Scully Scott Murphy and Presser

(57) ABSTRACT

The present disclosure provides a method of treating wound healing in a subject, the method comprising administering to the subject a compound that inhibits VEGF-B signalling.

10 Claims, 7 Drawing Sheets

Specification includes a Sequence Listing.

(56) References Cited

OTHER PUBLICATIONS

Wilgus T.A. et al., "Regulation of Scar Formation by Vascular Endothelial Growth Factor", Laboratory Investigation 88:579-590 (Jun. 2008).
Diabetes and Wound Healing, [online], 2007, [Retrieved on Aug. 17, 2018], Internet URL:http://www.ekinan-clinic.com/ishikaihou/28.html, together with a Partial English-Language translation.
English-language Translation of Japanese Notice of Reasons for Rejection dated Aug. 28, 2018 received in Japanese Patent Application No. 2016-541568.
European Examination Report dated Jun. 20, 2018 received in European Patent Application No. 14 871 427.2.
English-language Translation of Russian Office Action dated Feb. 2, 2018 received in Russian Patent Application No. 2016127196.

\* cited by examiner

- ● - *db/+* control treated
- ○ - *db/+* anti-Vegfb treated
- ■ - *db/db* control treated
- □ - *db/db* anti-Vegfb treated

- *db/+* control treated
- *db/db* control treated
- *db/db* anti-Vegfb treated

SEQUENCE LISTING

```
<160> NUMBER OF SEQ ID NOS: 46

<210> SEQ ID NO 1
<211> LENGTH: 207
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence

<400> SEQUENCE: 1

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 2
<211> LENGTH: 188
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence
```

-continued

<400> SEQUENCE: 2

```
Met Ser Pro Leu Leu Arg Arg Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

<210> SEQ ID NO 3
<211> LENGTH: 119
<212> TYPE: PRT
<213> ORGANISM: artificial
<220> FEATURE:
<223> OTHER INFORMATION: amino acid sequence from a VH of antibody 2H10

<400> SEQUENCE: 3

```
Val Gln Leu Gln Gln Pro Gly Thr Glu Leu Val Lys Pro Gly Ala Ser
1               5                   10                  15

Val Lys Leu Ser Cys Lys Ala Ser Gly Tyr Thr Phe Thr Gly Phe Trp
            20                  25                  30

Ile His Trp Val Lys Gln Arg Pro Gly Gln Gly Leu Glu Trp Ile Gly
            35                  40                  45

His Ile Asn Pro Gly Asn Gly Thr Asn Tyr Asn Glu Lys Phe Lys
50                  55                  60

Arg Met Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Ser Tyr Ser Asn Tyr Val Arg Ala Met Asp Tyr Trp Gly Gln Gly
            100                 105                 110

Thr Ser Val Thr Val Ser Ser
        115
```

<210> SEQ ID NO 4
<211> LENGTH: 106
<212> TYPE: PRT
<213> ORGANISM: artificial
<220> FEATURE:

<223> OTHER INFORMATION: amino acid sequence from a VL of antibody 2H10

<400> SEQUENCE: 4

```
Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Asn Phe Leu
            20                  25                  30

Asn Trp Tyr Gln Gln Lys Pro Asp Gly Thr Val Lys Leu Leu Ile Tyr
        35                  40                  45

Tyr Thr Ser Thr Leu His Ser Gly Val Pro Ser Arg Phe Ser Gly Ser
    50                  55                  60

Gly Ser Gly Thr Asp Tyr Ser Leu Thr Ile Ser Asn Leu Glu Gln Glu
65                  70                  75                  80

Asp Ile Ala Thr Tyr Phe Cys Gln Gln Gly Lys Thr Leu Pro Pro Thr
                85                  90                  95

Phe Gly Gly Gly Thr Lys Leu Glu Ile Lys
            100                 105
```

<210> SEQ ID NO 5
<211> LENGTH: 119
<212> TYPE: PRT
<213> ORGANISM: artificial
<220> FEATURE:
<223> OTHER INFORMATION: amino acid sequence from a VH of a humanized
      form of antibody 2H10

<400> SEQUENCE: 5

```
Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Gly Phe Trp
            20                  25                  30

Ile His Trp Val Arg Gln Ala Pro Gly Gln Gly Leu Glu Trp Met Gly
        35                  40                  45

His Ile Asn Pro Gly Asn Gly Thr Asn Tyr Asn Glu Lys Phe Lys
    50                  55                  60

Arg Arg Val Thr Met Thr Arg Asp Lys Ser Ile Ser Thr Ala Tyr Met
65                  70                  75                  80

Glu Leu Ser Arg Leu Arg Ser Asp Asp Thr Ala Val Tyr Tyr Cys Ala
                85                  90                  95

Arg Ser Tyr Ser Asn Tyr Val Arg Ala Met Asp Tyr Trp Gly Gln Gly
            100                 105                 110

Thr Leu Val Thr Val Ser Ser
        115
```

<210> SEQ ID NO 6
<211> LENGTH: 107
<212> TYPE: PRT
<213> ORGANISM: artificial
<220> FEATURE:
<223> OTHER INFORMATION: amino acid sequence of a VL of a humanized form
      of antibody 2H10

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45
```

Tyr Tyr Thr Ser Thr Leu His Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Lys Thr Leu Pro Pro
                 85                  90                  95

Thr Phe Gly Gly Gly Thr Lys Val Glu Ile Lys
            100                 105

<210> SEQ ID NO 7
<211> LENGTH: 116
<212> TYPE: PRT
<213> ORGANISM: artificial
<220> FEATURE:
<223> OTHER INFORMATION: amino acid sequence from a VH of antibody 4E12

<400> SEQUENCE: 7

Val Gln Pro Gln Gln Pro Gly Ala Glu Leu Val Lys Pro Gly Ala Ser
 1               5                  10                  15

Val Lys Met Ser Cys Lys Ala Ser Gly Asp Thr Phe Thr Asn Ser Trp
                20                  25                  30

Ile Gly Trp Val Thr Gln Arg Pro Gly Gln Gly Leu Glu Trp Ile Gly
             35                  40                  45

Asp Ile Phe Pro Gly Ser Gly His Thr Asn Tyr Asn Glu Lys Phe Lys
 50                  55                  60

Asn Arg Ala Thr Leu Thr Val Asp Thr Ser Ser Thr Ala Tyr Met
 65                  70                  75                  80

Leu Leu Ser Ser Leu Thr Ser Asp Asp Ser Ala Val Tyr Tyr Cys Val
                 85                  90                  95

Ile Glu Asn Tyr Ala Trp Phe Ala Tyr Trp Gly Gln Gly Thr Leu Val
            100                 105                 110

Thr Val Ser Ala
        115

<210> SEQ ID NO 8
<211> LENGTH: 107
<212> TYPE: PRT
<213> ORGANISM: artificial
<220> FEATURE:
<223> OTHER INFORMATION: amino acid sequence of a VL of antibody 4E12

<400> SEQUENCE: 8

Asp Ile Val Met Thr Gln Ser Gln Lys Phe Met Ser Ser Val Gly
 1               5                  10                  15

Asp Arg Val Ser Val Thr Cys Lys Ala Ser Gln Asn Val Asn Thr Asn
                20                  25                  30

Val Ala Trp Tyr Gln Gln Lys Gln Gly Gln Ser Pro Arg Pro Leu Ile
             35                  40                  45

Tyr Ser Ala Ser Ser Arg Cys Ser Gly Val Pro Asp Arg Phe Thr Gly
 50                  55                  60

Ser Gly Phe Gly Thr Asp Phe Thr Leu Thr Ile Ser Asn Val Gln Ser
 65                  70                  75                  80

Glu Asp Leu Ala Glu Tyr Phe Cys Gln Gln Tyr His Ser Phe Pro Leu
                 85                  90                  95

Thr Phe Gly Ala Gly Ala Lys Leu Asp Leu Lys
            100                 105

```
<210> SEQ ID NO 9
<211> LENGTH: 118
<212> TYPE: PRT
<213> ORGANISM: artificial
<220> FEATURE:
<223> OTHER INFORMATION: amino acid sequence from a VH of antibody 2F5

<400> SEQUENCE: 9

Val Gln Leu Gln Gln Ser Gly Pro Glu Leu Val Lys Pro Gly Thr Ser
1               5                   10                  15

Val Arg Ile Ser Cys Lys Ala Ser Gly Tyr Thr Phe Thr Thr Phe Tyr
            20                  25                  30

Ile His Trp Val Lys Gln Arg Pro Gly Gln Gly Leu Glu Trp Ile Gly
        35                  40                  45

Trp Phe Tyr Pro Gly Asn Val Asn Thr Asn Tyr Asn Glu Lys Leu Lys
    50                  55                  60

Gly Lys Ala Thr Leu Thr Ala Asp Lys Ser Ser Ser Ala Ala Tyr Leu
65                  70                  75                  80

Gln Leu Asn Ser Leu Thr Ser Glu Asp Ser Ala Val Tyr Phe Cys Thr
                85                  90                  95

Arg Ser Pro Tyr Tyr Gly Tyr Val Phe Asp Tyr Trp Gly Gln Gly Thr
            100                 105                 110

Thr Leu Thr Val Ser Ser
        115

<210> SEQ ID NO 10
<211> LENGTH: 107
<212> TYPE: PRT
<213> ORGANISM: artificial
<220> FEATURE:
<223> OTHER INFORMATION: amino acid sequence of a VL of antibody 2F5

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Ser Leu Thr
                85                  90                  95

Phe Gly Ala Gly Ala Thr Lys Leu Glu Leu Lys
            100                 105

<210> SEQ ID NO 11
<211> LENGTH: 33
<212> TYPE: DNA
<213> ORGANISM: Artificial Sequence
<220> FEATURE:
<223> OTHER INFORMATION: Nucleotide sequence of 2H10 VL CDR1

<400> SEQUENCE: 11
agggcaagtc aggacattag caattttta aac                                      33

<210> SEQ ID NO 12
<211> LENGTH: 21
```

<212> TYPE: DNA
<213> ORGANISM: Artificial Sequence
<220> FEATURE:
<223> OTHER INFORMATION: Nucleotide sequence of 2H10 VL CDR2

<400> SEQUENCE: 12
tacacatcaa cattacactc a                                              21

<210> SEQ ID NO 13
<211> LENGTH: 27
<212> TYPE: DNA
<213> ORGANISM: Artificial Sequence
<220> FEATURE:
<223> OTHER INFORMATION: Nucleotide sequence of 2H10 VL CDR3

<400> SEQUENCE: 13
caacagggta aaacgcttcc tcccacg                                        27

<210> SEQ ID NO 14
<211> LENGTH: 30
<212> TYPE: DNA
<213> ORGANISM: Artificial Sequence
<220> FEATURE:
<223> OTHER INFORMATION: Nucleotide sequence of 2H10 VH CDR1

<400> SEQUENCE: 14
ggctacactt tcactggctt ctggatacac                                     30

<210> SEQ ID NO 15
<211> LENGTH: 51
<212> TYPE: DNA
<213> ORGANISM: Artificial Sequence
<220> FEATURE:
<223> OTHER INFORMATION: Nucleotide sequence of 2H10 VH CDR2

<400> SEQUENCE: 15
catattaatc ctggcaatgg tggcactaac tacaatgaga agttcaagag a              51

<210> SEQ ID NO 16
<211> LENGTH: 33
<212> TYPE: DNA
<213> ORGANISM: Artificial Sequence
<220> FEATURE:
<223> OTHER INFORMATION: Nucleotide sequence of 2H10 VH CDR3

<400> SEQUENCE: 16
tcctatagta actacgtgcg ggctatggac tac                                 33

<210> SEQ ID NO 17
<211> LENGTH: 11
<212> TYPE: PRT
<213> ORGANISM: Artificial Sequence
<220> FEATURE:
<223> OTHER INFORMATION: Amino acid sequence of 2H10 VL CDR1

<400> SEQUENCE: 17

Arg Ala Ser Gln Asp Ile Ser Asn Phe Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: amino acid sequence of 2H10 VL CDR2

<400> SEQUENCE: 18

-continued

```
Tyr Thr Ser Thr Leu His Ser
1               5

<210> SEQ ID NO 19
<211> LENGTH: 9
<212> TYPE: PRT
<213> ORGANISM: Artificial Sequence
<220> FEATURE:
<223> OTHER INFORMATION: amino acid sequence of 2H10 VL CDR3

<400> SEQUENCE: 19

Gln Gln Gly Lys Thr Leu Pro Pro Thr
1               5

<210> SEQ ID NO 20
<211> LENGTH: 10
<212> TYPE: PRT
<213> ORGANISM: Artificial Sequence
<220> FEATURE:
<223> OTHER INFORMATION: amino acid sequence of 2H10 VH CDR1

<400> SEQUENCE: 20

Gly Tyr Thr Phe Thr Gly Phe Trp Ile His
1               5                   10

<210> SEQ ID NO 21
<211> LENGTH: 17
<212> TYPE: PRT
<213> ORGANISM: Artificial Sequence
<220> FEATURE:
<223> OTHER INFORMATION: amino acid sequence of 2H10 VH CDR2

<400> SEQUENCE: 21

His Ile Asn Pro Gly Asn Gly Gly Thr Asn Tyr Asn Glu Lys Phe Lys
1               5                   10                  15

Arg

<210> SEQ ID NO 22
<211> LENGTH: 11
<212> TYPE: PRT
<213> ORGANISM: Artificial Sequence
<220> FEATURE:
<223> OTHER INFORMATION: amino acid sequence of 2H10 VH CDR3

<400> SEQUENCE: 22

Ser Tyr Ser Asn Tyr Val Arg Ala Met Asp Tyr
1               5                   10

<210> SEQ ID NO 23
<211> LENGTH: 33
<212> TYPE: DNA
<213> ORGANISM: Artificial Sequence
<220> FEATURE:
<223> OTHER INFORMATION: nucleotide sequence of 2F5 VL CDR1

<400> SEQUENCE: 23
aaggccagtc aggatgtggg tactgctgta gcc                               33

<210> SEQ ID NO 24
<211> LENGTH: 21
<212> TYPE: DNA
<213> ORGANISM: Artificial Sequence
<220> FEATURE:
<223> OTHER INFORMATION: nucleotide sequence of 2F5 VL CDR2

<400> SEQUENCE: 24
```

```
tgggcatcca cccggcacac t                                              21

<210> SEQ ID NO 25
<211> LENGTH: 24
<212> TYPE: DNA
<213> ORGANISM: Artificial Sequence
<220> FEATURE:
<223> OTHER INFORMATION: nucleotide sequence of 2F5 VL CDR3

<400> SEQUENCE: 25
caacaatata gcagctctct cacg                                           24

<210> SEQ ID NO 26
<211> LENGTH: 30
<212> TYPE: DNA
<213> ORGANISM: Artificial Sequence
<220> FEATURE:
<223> OTHER INFORMATION: nucleotide sequence of 2F5 VH CDR1

<400> SEQUENCE: 26
ggctacacct tcacaacctt ctatatacac                                     30

<210> SEQ ID NO 27
<211> LENGTH: 51
<212> TYPE: DNA
<213> ORGANISM: Artificial Sequence
<220> FEATURE:
<223> OTHER INFORMATION: nucleotide sequence of 2F5 VH CDR2

<400> SEQUENCE: 27 tggtttatc ctggaaatgt taataccaac tacaatgaga agctcaaggg c              51

<210> SEQ ID NO 28
<211> LENGTH: 30
<212> TYPE: DNA
<213> ORGANISM: Artificial Sequence
<220> FEATURE:
<223> OTHER INFORMATION: nucleotide sequence of 2F5 VH CDR3

<400> SEQUENCE: 28
tccccttact acggctacgt ttttgactac                                     30

<210> SEQ ID NO 29
<211> LENGTH: 11
<212> TYPE: PRT
<213> ORGANISM: Artificial Sequence
<220> FEATURE:
<223> OTHER INFORMATION: amino acid sequence of 2F5 VL CDR1

<400> SEQUENCE: 29

Lys Ala Ser Gln Asp Val Gly Thr Ala Val Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: amino acid sequence of 2F5 VL CDR2

<400> SEQUENCE: 30

Trp Ala Ser Thr Arg His Thr
1               5

<210> SEQ ID NO 31
```

```
<211> LENGTH: 8
<212> TYPE: PRT
<213> ORGANISM: Artificial Sequence
<220> FEATURE:
<223> OTHER INFORMATION: amino acid sequence of 2F5 VL CDR3

<400> SEQUENCE: 31

Gln Gln Tyr Ser Ser Ser Leu Thr
1               5

<210> SEQ ID NO 32
<211> LENGTH: 10
<212> TYPE: PRT
<213> ORGANISM: Artificial Sequence
<220> FEATURE:
<223> OTHER INFORMATION: amino acid sequence of 2F5 VH CDR1

<400> SEQUENCE: 32

Gly Tyr Thr Phe Thr Thr Phe Tyr Ile His
1               5                   10

<210> SEQ ID NO 33
<211> LENGTH: 17
<212> TYPE: PRT
<213> ORGANISM: Artificial Sequence
<220> FEATURE:
<223> OTHER INFORMATION: amino acid sequence of 2F5 VH CDR2

<400> SEQUENCE: 33

Trp Phe Tyr Pro Gly Asn Val Asn Thr Asn Tyr Asn Glu Lys Leu Lys
1               5                   10                  15

Gly

<210> SEQ ID NO 34
<211> LENGTH: 10
<212> TYPE: PRT
<213> ORGANISM: Artificial Sequence
<220> FEATURE:
<223> OTHER INFORMATION: amino acid sequence of 2F5 VH CDR3

<400> SEQUENCE: 34

Ser Pro Tyr Tyr Gly Tyr Val Phe Asp Tyr
1               5                   10

<210> SEQ ID NO 35
<211> LENGTH: 33
<212> TYPE: DNA
<213> ORGANISM: Artificial Sequence
<220> FEATURE:
<223> OTHER INFORMATION: nucleotide sequence of 4E12 VL CDR1

<400> SEQUENCE: 35
aaggccagtc agaatgtgaa cactaatgta gcc                                    33

<210> SEQ ID NO 36
<211> LENGTH: 21
<212> TYPE: DNA
<213> ORGANISM: Artificial Sequence
<220> FEATURE:
<223> OTHER INFORMATION: nucleotide sequence of 4E12 VL CDR2

<400> SEQUENCE: 36
tcggcatcct cccggtgcag t                                                 21

<210> SEQ ID NO 37
<211> LENGTH: 27
```

```
<212> TYPE: DNA
<213> ORGANISM: Artificial Sequence
<220> FEATURE:
<223> OTHER INFORMATION: nucleotide sequence of 4E12 VL CDR3

<400> SEQUENCE: 37
cagcaatatc acagctttcc gctcacg                                          27

<210> SEQ ID NO 38
<211> LENGTH: 30
<212> TYPE: DNA
<213> ORGANISM: Artificial Sequence
<220> FEATURE:
<223> OTHER INFORMATION: nucleotide sequence of 4E12 VH CDR1

<400> SEQUENCE: 38
ggcgacacct tcaccaactc ctggataggc                                       30

<210> SEQ ID NO 39
<211> LENGTH: 51
<212> TYPE: DNA
<213> ORGANISM: Artificial Sequence
<220> FEATURE:
<223> OTHER INFORMATION: nucleotide sequence of 4E12 VH CDR2

<400> SEQUENCE: 39
gatatttttc tgggagtgg tcatactaac tacaatgaga agttcaagaa c                51

<210> SEQ ID NO 40
<211> LENGTH: 24
<212> TYPE: DNA
<213> ORGANISM: Artificial Sequence
<220> FEATURE:
<223> OTHER INFORMATION: nucleotide sequence of 4E12 VH CDR3

<400> SEQUENCE: 40
gagaattatg cctggtttgc ttat                                             24

<210> SEQ ID NO 41
<211> LENGTH: 11
<212> TYPE: PRT
<213> ORGANISM: Artificial Sequence
<220> FEATURE:
<223> OTHER INFORMATION: amino acid sequence of 4E12 VL CDR1

<400> SEQUENCE: 41

Lys Ala Ser Gln Asn Val Asn Thr Asn Val Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: amino acid sequence of 4E12 VL CDR2

<400> SEQUENCE: 42

Ser Ala Ser Ser Arg Cys Ser
1               5

<210> SEQ ID NO 43
<211> LENGTH: 9
<212> TYPE: PRT
<213> ORGANISM: Artificial Sequence
<220> FEATURE:
<223> OTHER INFORMATION: amino acid sequence of 4E12 VL CDR3
```

```
<400> SEQUENCE: 43

Gln Gln Tyr His Ser Phe Pro Leu Thr
1               5

<210> SEQ ID NO 44
<211> LENGTH: 10
<212> TYPE: PRT
<213> ORGANISM: Artificial Sequence
<220> FEATURE:
<223> OTHER INFORMATION: amino acid sequence of 4E12 VH CDR1

<400> SEQUENCE: 44

Gly Asp Thr Phe Thr Asn Ser Trp Ile Gly
1               5                   10

<210> SEQ ID NO 45
<211> LENGTH: 17
<212> TYPE: PRT
<213> ORGANISM: Artificial Sequence
<220> FEATURE:
<223> OTHER INFORMATION: amino acid sequence of 4E12 VH CDR2

<400> SEQUENCE: 45

Asp Ile Phe Pro Gly Ser Gly His Thr Asn Tyr Asn Glu Lys Phe Lys
1               5                   10                  15

Asn

<210> SEQ ID NO 46
<211> LENGTH: 8
<212> TYPE: PRT
<213> ORGANISM: Artificial Sequence
<220> FEATURE:
<223> OTHER INFORMATION: amino acid sequence of 4E12 VH CDR3

<400> SEQUENCE: 46

Glu Asn Tyr Ala Trp Phe Ala Tyr
1               5
```

METHODS OF TREATING WOUNDS IN A DIABETIC SUBJECT

RELATED APPLICATION DATA

The present application claims priority from Australian Patent Application No. 2013904942 entitled "Method of Treating Wounds" filed on 18 Dec. 2013 and from Australian Patent Application No. 2013904966 entitled "Method of Treating Wounds" filed on 19 Dec. 2013. The entire contents of both applications are hereby incorporated by reference.

SEQUENCE LISTING

The present application is filed with a Sequence Listing in electronic form. The entire contents of the Sequence Listing are hereby incorporated by reference.

FIELD

The present application relates to a method for treating or preventing wounds.

INTRODUCTION

Wound healing is a complex process, involving a coagulation phase, an inflammation phase, a granulation tissue formation phase, and a tissue remodeling phase. These events are triggered by cytokines and growth factors that are released at the site of injury. Many factors can complicate or interfere with normal adequate wound healing. For example, such factors include age, infection, poor nutrition, immunosuppression, medications, radiation, diabetes, peripheral vascular disease, systemic illness, smoking, stress, etc.

Chronic wounds are those that do not proceed through an orderly and timely repair process to produce anatomic and functional integrity. Chronic wounds are estimated to affect 5.7 million patients and cost about US$20 billion annually in the United States alone.

For patients with diabetes, which is a chronic, debilitating disease that affected approximately 347 million people in the United States in 2008, development of a diabetic foot ulcer (also referred to as a wound or, in some cases a chronic wound) is a common complication. Because the skin serves as the primary barrier again the environment, an open refractory wound can be catastrophic; a major disability (including limb loss) and even death can result. Foot ulceration is the precursor to about 85% of lower extremity amputations in people with diabetes.

In diabetes any of phases of wound healing can be disrupted. However, a key feature of diabetic wounds is an imbalance in the synthesis and degradation of extracellular matrix proteins. Moreover, chronic inflammation causes a delay in the formation of mature granulation tissue and a reduction in wound tensile strength.

Current wound care therapies include surgical and medical approaches. Medication aims to control or prevent infections, prevent ischemia and edema, reduce pain and improve metabolic status. Local treatments include topical application of e.g. growth factors and platelet-rich plasma and wound dressings of e.g. hydrocolloids and hydrogels. Surgical interventions include angioplasty, skin grafts and mechanical support to decrease pressure. Each therapy suffers from its own disadvantages, such as a crucial need for intervening in the right healing phase, disappointing efficacy and high cost. Thus, there is a need in the art for improved treatments for wounds.

SUMMARY

In producing the present invention, the inventors studied the effects of inhibiting signaling of vascular endothelial growth factor B (VEGF-B) in an accepted mouse model of wounding, e.g., diabetic wounds. The inventors studied the effect of this growth factor by administering an antagonist of VEGF-B (e.g., an antagonistic antibody) to diabetic mice in which a wound had been induced. The inventors found that inhibition of VEGF-B resulted in significantly more rapid wound closure and healing. The inventors also found that this improved wound healing was particularly noticeable in the early phases of wound closure, e.g., when the wound is largest and open). In some cases (e.g., in an experiment described herein) the changes in wound healing occurred despite a moderate effect on blood glucose levels in diabetic subjects, indicating that inhibiting VEGF-B provides a wound healing benefit through a pathway additional to or other than glycemic control.

The findings by the inventors provide the basis for methods for inducing or enhancing wound healing or in treating wounds or in slowing or preventing complications of wounds in a subject by inhibiting VEGF-B signaling. For example, the present disclosure provides a method for treating wounds in a subject, the method comprising administering to the subject a compound that inhibits VEGF-B signaling.

In another example, the disclosure provides a method for inducing or enhancing wound healing in a subject, the method comprising administering to the subject a compound that inhibits VEGF-B signaling.

Assessment of wound healing can be determined, e.g., by the percentage reduction in the wound area, or complete wound closure. The wound area can be determined by quantitative analysis, e.g., area measurements of the wound, planimetric tracings of the wound, etc. Complete wound closure can be determined by, e.g., skin closure without drainage or dressing requirements. Photographs of the wound, physical examinations of the wound, etc. can also be used to assess wound healing. Acceleration of wound healing can be expressed in terms of percent acceleration or expressed in terms of a Hazard ratio as a time to healing.

In another example, the disclosure provides a method for preventing or slowing progression of a wound or a complication of a wound, the method comprising administering to the subject a compound that inhibits VEGF-B signaling.

In one example, the wound is acute or normal, e.g., thermal injury (e.g., a burn), trauma, surgery, excision of extensive skin cancer, deep fungal and bacterial infections, vasculitis or scleroderma.

In another example, the wound is chronic. For example, the wound is an arterial ulcer, a diabetic wound, a diabetic ulcer, a pressure ulcer or a venous ulcer.

In one example, the wound is a dermal wound.

In one example, the subject suffers from obesity and/or diabetes.

For example, the subject suffers from diabetes, e.g., type 1 or type 2 diabetes. In such a case, the wound may be referred to as a diabetic wound (i.e., a wound in a diabetic subject) or a diabetic ulcer (i.e., an ulcer in a diabetic subject). For example, the wound is a diabetic foot ulcer or a diabetic leg ulcer.

In one example, the wound is a decubitus ulcer.

In one example, the subject suffers from one or more of neuropathy (e.g., diabetic neuropathy), peripheral vascular disease, poor glycemic control, previous foot ulcerations or amputations, nephropathy (or diabetic nephropathy), ischemia of small and large blood vessels or poor visual acuity.

In one example, the subject has a wound.

In another example, the subject is at risk of developing a wound (e.g., a chronic wound) and is administered the compound prior to, e.g., surgery (when a wound will be induced). For example, the disclosure provides a method for reducing the severity of a wound, e.g., an induced wound, e.g., induced by surgery.

As exemplified herein, inhibition of VEGF-B signaling is effective in the treatment of diabetic wounds. Thus, in one example, the disclosure provides a method for treating a wound in a diabetic subject, the method comprising administering to the subject a compound that inhibits VEGF-B signaling.

The present disclosure also provides a method for enhancing or inducing wound healing in a diabetic subject suffering from a wound, the method comprising administering to the subject a compound that inhibits VEGF-B signaling.

In one example, the subject is at risk of a wound progressing. For example, the subject suffers from diabetes. For example, the subject suffers from diabetes and one or more of diabetic neuropathy, peripheral vascular disease, poor glycemic control, previous foot ulcerations or amputations, nephropathy (or diabetic nephropathy), ischemia of small and large blood vessels or poor visual acuity.

In one example, the present disclosure provides a method for reducing or preventing progression of a wound in a diabetic subject, the method comprising administering to the subject a compound that inhibits VEGF-B signaling.

In another example, the present disclosure provides a method for reducing the risk that a subject (e.g., a diabetic subject) suffering from a wound will require an amputation, the method comprising administering to the subject a compound that inhibits VEGF-B signaling.

In one example, the compound is administered in an amount effective to have one or more of the following effects:

Enhance the rate of wound closure compared to the rate in a subject (e.g., in a subject suffering from diabetes and a wound) to whom the compound has not been administered; and/or Enhance the amount of wound closure at a specific point in time (e.g., following commencement of treatment) compared to the rate in a subject (e.g., in a subject suffering from diabetes and a wound) to whom the compound has not been administered; and/or Enhance maturation of blood vessels in a subject compared to in a subject (e.g., in a subject suffering from diabetes and a wound) to whom the compound has not been administered.

The present disclosure also provides a method for having one or more of the following effects in a subject, the method comprising administering to the subject who has suffered from a wound (and, optionally suffers from diabetes) a compound that inhibits VEGF-B signalling:

Enhancing the rate of wound closure compared to the rate in a subject to whom the compound has not been administered; and/or Enhance the amount of wound closure at a specific point in time compared to the rate in a subject to whom the compound has not been administered; and/or Enhance maturation of blood vessels in a subject compared to in a subject to whom the compound has not been administered In one example, the compound that inhibits VEGF-B signaling specifically inhibits VEGF-B signaling. This does not mean that a method of the present disclosure does not encompass inhibiting signaling of multiple VEGF proteins, only that the compound (or part thereof) that inhibits VEGF-B signaling is specific to VEGF-B, e.g., is not a general inhibitor of VEGF proteins. This term also does not exclude, e.g., a bispecific antibody or protein comprising binding domains thereof, which can specifically inhibit VEGF-B signaling with one (or more) binding domains and can specifically inhibit signaling of another protein with another binding domain.

In one example, a compound that inhibits VEGF-B signaling binds to VEGF-B. For example, the compound is a protein comprising an antibody variable region that binds to or specifically binds to VEGF-B and neutralizes VEGF-B signaling.

In one example, the compound is an antibody mimetic. For example, the compound is a protein comprising an antigen binding domain of an immunoglobulin, e.g., an IgNAR, a camelid antibody or a T cell receptor.

In one example, a compound is a domain antibody (e.g., comprising only a heavy chain variable region or only a light chain variable region that binds to VEGF-B) or a heavy chain only antibody (e.g., a camelid antibody or an IgNAR) or variable region thereof.

In one example, a compound is a protein comprising a Fv. For example, the protein is selected from the group consisting of:

(i) a single chain Fv fragment (scFv);
(ii) a dimeric scFv (di-scFv); or
(iv) a diabody;
(v) a triabody;
(vi) a tetrabody;
(vii) a Fab;
(viii) a F(ab')$_2$;
(ix) a Fv; or
(x) one of (i) to (ix) linked to a constant region of an antibody, Fc or a heavy chain constant domain ($C_H$)2 and/or $C_H$3.

In another example, a compound is an antibody. Exemplary antibodies are full-length and/or naked antibodies.

In one example, the compound is a protein that is recombinant, chimeric, CDR grafted, humanized, synhumanized, primatized, deimmunized or human.

In one example, the compound is a protein comprising an antibody variable region that competitively inhibits the binding of antibody 2H10 to VEGF-B. In one example, the protein comprises a heavy chain variable region ($V_H$) comprising a sequence set forth in SEQ ID NO: 3 and a light chain variable region ($V_L$) comprising a sequence set forth in SEQ ID NO: 4.

In one example, the compound is a protein comprising a humanized variable region of antibody 2H10. For example, the protein comprises a variable region comprising the complementarity determining regions (CDRs) of the $V_H$ and/or the $V_L$ of antibody 2H10. For example, the protein comprises:

(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and/or
(ii) a $V_L$ comprising:
  (a) a CDR1 comprising a sequence set forth in amino acids 23-33 of SEQ ID NO: 4;

(b) a CDR2 comprising a sequence set forth in amino acids 49-55 of SEQ ID NO: 4; and
(c) a CDR3 comprising a sequence set forth in amino acids 88-96 of SEQ ID NO: 4.

In one example, the compound is a protein comprising a $V_H$ and a $V_L$, the $V_H$ and $V_L$ being humanized variable regions of antibody 2H10. For example, the protein comprises:
(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and
(ii) a $V_L$ comprising:
  (a) a CDR1 comprising a sequence set forth in amino acids 23-33 of SEQ ID NO: 4;
  (b) a CDR2 comprising a sequence set forth in amino acids 49-55 of SEQ ID NO: 4; and
  (c) a CDR3 comprising a sequence set forth in amino acids 88-96 of SEQ ID NO: 4.

In one example, the variable region or $V_H$ in any of the foregoing paragraphs comprises a sequence set forth in SEQ ID NO: 5.

In one example, the variable region or $V_L$ in any of the foregoing paragraphs comprises a sequence set forth in SEQ ID NO: 6.

In one example, the compound is an antibody.

In one example, the compound is an antibody comprising a $V_H$ comprising a sequence set forth in SEQ ID NO: 5 and a $V_L$ comprising a sequence set forth in SEQ ID NO: 6.

In one example, the protein or antibody is any form of the protein or antibody encoded by a nucleic acid encoding any of the foregoing proteins or antibodies or a cell expressing the protein or antibody (e.g., including a post-translationally modified protein or antibody).

In one example, the protein or antibody comprises:
(i) a $V_H$ comprising:
  (a) a CDR1 comprising a sequence encoded by a nucleic acid comprising SEQ ID NO: 11 or comprising an amino acid sequence of SEQ ID NO: 17;
  (b) a CDR2 comprising a sequence encoded by a nucleic acid comprising SEQ ID NO: 12 or comprising an amino acid sequence of SEQ ID NO: 18; and
  (c) a CDR3 comprising a sequence encoded by a nucleic acid comprising SEQ ID NO: 13 or comprising an amino acid sequence of SEQ ID NO: 19; and/or
(ii) a $V_L$ comprising:
  (a) a CDR1 comprising a sequence encoded by a nucleic acid comprising SEQ ID NO: 14 or comprising an amino acid sequence of SEQ ID NO: 20;
  (b) a CDR2 comprising a sequence encoded by a nucleic acid comprising SEQ ID NO: 15 or comprising an amino acid sequence of SEQ ID NO: 21; and
  (c) a CDR3 comprising a sequence encoded by a nucleic acid comprising SEQ ID NO: 16 or comprising an amino acid sequence of SEQ ID NO: 22.

In one example, the protein or antibody comprises:
(i) a $V_H$ comprising:
  (a) a CDR1 comprising a sequence encoded by a nucleic acid comprising SEQ ID NO: 23 or comprising an amino acid sequence of SEQ ID NO: 29;
  (b) a CDR2 comprising a sequence encoded by a nucleic acid comprising SEQ ID NO: 24 or comprising an amino acid sequence of SEQ ID NO: 30; and
  (c) a CDR3 comprising a sequence encoded by a nucleic acid comprising SEQ ID NO: 25 or comprising an amino acid sequence of SEQ ID NO: 31; and/or
(ii) a $V_L$ comprising:
  (a) a CDR1 comprising a sequence encoded by a nucleic acid comprising SEQ ID NO: 26 or comprising an amino acid sequence of SEQ ID NO: 32;
  (b) a CDR2 comprising a sequence encoded by a nucleic acid comprising SEQ ID NO: 27 or comprising an amino acid sequence of SEQ ID NO: 33; and
  (c) a CDR3 comprising a sequence encoded by a nucleic acid comprising SEQ ID NO: 28 or comprising an amino acid sequence of SEQ ID NO: 34.

In one example, the protein or antibody comprises:
(i) a $V_H$ comprising:
  (a) a CDR1 comprising a sequence encoded by a nucleic acid comprising SEQ ID NO: 35 or comprising an amino acid sequence of SEQ ID NO: 41;
  (b) a CDR2 comprising a sequence encoded by a nucleic acid comprising SEQ ID NO: 36 or comprising an amino acid sequence of SEQ ID NO: 42; and
  (c) a CDR3 comprising a sequence encoded by a nucleic acid comprising SEQ ID NO: 37 or comprising an amino acid sequence of SEQ ID NO: 43; and/or
(ii) a $V_L$ comprising:
  (a) a CDR1 comprising a sequence encoded by a nucleic acid comprising SEQ ID NO: 38 or comprising an amino acid sequence of SEQ ID NO: 44;
  (b) a CDR2 comprising a sequence encoded by a nucleic acid comprising SEQ ID NO: 39 or comprising an amino acid sequence of SEQ ID NO: 45; and
  (c) a CDR3 comprising a sequence encoded by a nucleic acid comprising SEQ ID NO: 40 or comprising an amino acid sequence of SEQ ID NO: 46.

In one example, the compound is within a composition. For example, the composition comprises a protein comprising an antibody variable region or a $V_H$ or a $V_L$ or an antibody as described herein. In one example, the composition additionally comprises one or more variants (e.g., post-translationally modified variants) of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparagine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

In one example, the compound that inhibits VEGF-B signaling inhibits or prevents expression of VEGF-B. For example, the compound is selected from the group an antisense, a siRNA, a RNAi, a ribozyme and a DNAzyme.

In one example, the VEGF-B is mammalian VEGF-B. e.g., human VEGF-B.

In one example, the subject is a mammal, for example a primate, such as a human.

Methods of treatment described herein can additionally comprise administering a further treatment for a wound.

Methods of treatment of diabetic wounds or ulcers described herein can additionally comprise administering a further compound to treat or prevent (or delay progression of) diabetes. Exemplary compounds are described herein.

In another example, the disclosure provides a compound that inhibits VEGF-B signaling for inducing or enhancing wound healing in a subject and/or preventing or slowing progression of a wound or a complication of a wound in a subject.

In another example, the disclosure provides for use of a compound that inhibits VEGF-B signaling in the manufacture of a medicament for inducing or enhancing wound healing in a subject and/or preventing or slowing progression of a wound or a complication of a wound in a subject.

The present disclosure also provides a kit comprising a compound that inhibits VEGF-B signaling packaged with instructions for use in the treatment or prevention of a wound and/or a method of the disclosure.

Exemplary wounds and compounds are described herein and are to be taken to apply mutatis mutandis to the examples of the disclosure set out in the previous three paragraphs.

Examples of the present disclosure shall be taken to apply mutatis mutandis to improving wound healing or reducing recurrence or the likelihood of recurrence of a wound (e.g., a diabetic ulcer) or accelerating wound healing.

BRIEF DESCRIPTION OF THE DRAWINGS

FIG. 1A shows Fed blood glucose levels and FIG. 1B shows fed body weight in diabetic db/db or non-diabetic db/+ control or anti-VEGF-B treated mice before and after wounding of the animals (n=4-7/group) Values are means±s.e.m.

FIG. 3A shows fed blood glucose levels (n=5-6/group) and FIG. 3B shows wound closure over the first four days (n=10-12/group). Values are means±s.e.m. ***P<0.001 compared to db/db control treated.

FIG. 5A shows quantification of Brdu/DAPI staining and FIG. 5B shows quantification of CD45, CIV and CD31 staining from db/db mice with control or 2H10 antibody. n=4-6/group. Values are average ±s.e.m. * P<0.05, ** P<0.01 compared to db/db control treated.

KEY TO SEQUENCE LISTING

Figure 1A:
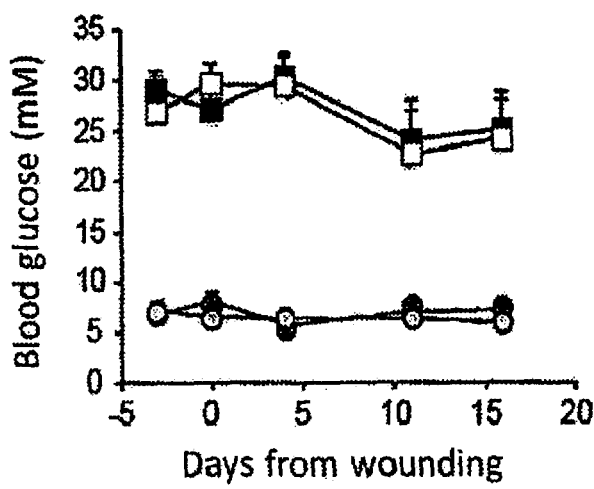
FIGS. 1A and 1B depict a series of graphical representations showing anti-VEGF-B treatment, using 2H10 does not significantly affect blood glucose levels or weight loss upon wounding in a severely diabetic animal model.

SEQ ID NO: 1 is an amino acid sequence of a human VEGF-B$_{186}$ isoform containing a 21 amino acid N-terminal signal sequence SEQ ID NO: 2 is an amino acid sequence of a human VEGF-B$_{167}$ isoform containing a 21 amino acid N-terminal signal sequence SEQ ID NO: 3 is an amino acid sequence from a $V_H$ of antibody 2H10.

SEQ ID NO: 4 is an amino acid sequence from a $V_L$ of antibody 2H10.

SEQ ID NO: 5 is an amino acid sequence from a $V_H$ of a humanized form of antibody 2H10.

SEQ ID NO: 6 is an amino acid sequence of a $V_L$ of a humanized form of antibody 2H10.

SEQ ID NO: 7 is an amino acid sequence from a $V_H$, of antibody 4E12.

SEQ ID NO: 8 is an amino acid sequence of a $V_L$ of antibody 4E12.

SEQ ID NO: 9 is an amino acid sequence from a $V_H$ of antibody 2F5.

SEQ ID NO: 10 is an amino acid sequence of a $V_L$ of antibody 2F5.

SEQ ID NO: 11 is a nucleotide sequence from a $V_L$ CDR1 of antibody 2H10

SEQ ID NO: 12 is a nucleotide sequence from a $V_L$ CDR2 of antibody 2H10

SEQ ID NO: 13 is a nucleotide sequence from a $V_L$ CDR3 of antibody 2H10

SEQ ID NO: 14 is a nucleotide sequence from a $V_H$ CDR1 of antibody 2H10

SEQ ID NO: 15 is a nucleotide sequence from a $V_H$ CDR2 of antibody 2H10

SEQ ID NO: 16 is a nucleotide sequence from a $V_H$ CDR3 of antibody 2H10

SEQ ID NO: 17 is an amino acid sequence from a $V_L$ CDR1 of antibody 2H10

SEQ ID NO: 18 is an amino acid sequence from a $V_L$ CDR2 of antibody 2H10

SEQ ID NO: 19 is an amino acid sequence from a $V_L$ CDR3 of antibody 2H10

SEQ ID NO: 20 is an amino acid sequence from a $V_H$ CDR1 of antibody 2H10

SEQ ID NO: 21 is an amino acid sequence from a $V_H$ CDR2 of antibody 2H10

SEQ ID NO: 22 is an amino acid sequence from a $V_H$ CDR3 of antibody 2H10

SEQ ID NO: 23 is a nucleotide sequence from a $V_L$ CDR1 of antibody 2F5

SEQ ID NO: 24 is a nucleotide sequence from a $V_L$ CDR2 of antibody 2F5

SEQ ID NO: 25 is a nucleotide sequence from a $V_L$ CDR3 of antibody 2F5

SEQ ID NO: 26 is a nucleotide sequence from a $V_H$ CDR1 of antibody 2F5

SEQ ID NO: 27 is a nucleotide sequence from a $V_H$ CDR2 of antibody 2F5

SEQ ID NO: 28 is a nucleotide sequence from a $V_H$ CDR3 of antibody 2F5

SEQ ID NO: 29 is an amino acid sequence from a $V_L$ CDR1 of antibody 2F5

SEQ ID NO: 30 is an amino acid sequence from a $V_L$ CDR2 of antibody 2F5

SEQ ID NO: 31 is an amino acid sequence from a $V_L$ CDR3 of antibody 2F5

SEQ ID NO: 32 is an amino acid sequence from a $V_H$ CDR1 of antibody 2F5

SEQ ID NO: 33 is an amino acid sequence from a $V_H$ CDR2 of antibody 2F5

SEQ ID NO: 34 is an amino acid sequence from a $V_H$ CDR3 of antibody 2F5

SEQ ID NO: 35 is a nucleotide sequence from a $V_L$ CDR1 of antibody 4E12

SEQ ID NO: 36 is a nucleotide sequence from a $V_L$ CDR2 of antibody 4E12

SEQ ID NO: 37 is a nucleotide sequence from a $V_L$ CDR3 of antibody 4E12

SEQ ID NO: 38 is a nucleotide sequence from a $V_H$ CDR1 of antibody 4E12

SEQ ID NO: 39 is a nucleotide sequence from a $V_H$ CDR2 of antibody 4E12

SEQ ID NO: 40 is a nucleotide sequence from a $V_H$ CDR3 of antibody 4E12

SEQ ID NO: 41 is an amino acid sequence from a $V_L$ CDR1 of antibody 4E12

SEQ ID NO: 42 is an amino acid sequence from a $V_L$ CDR2 of antibody 4E12

SEQ ID NO: 43 is an amino acid sequence from a $V_L$ CDR3 of antibody 4E12

SEQ ID NO: 44 is an amino acid sequence from a $V_H$ CDR1 of antibody 4E12

SEQ ID NO: 45 is an amino acid sequence from a $V_H$ CDR2 of antibody 4E12

SEQ ID NO: 46 is an amino acid sequence from a $V_H$ CDR3 of antibody 4E12

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984). J. Sambrook et al. Molecular Cloning: A Laboratory Manual, Cold Spring Harbor Laboratory Press (1989), T. A. Brown (editor). Essential Molecular Biology: A Practical Approach. Volumes 1 and 2, IRL Press (1991), D. M. Glover and B. D. Hames (editors), DNA Cloning: A Practical Approach, Volumes 1-4. IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual. Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991. Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

Any discussion of a protein or antibody herein will be understood to include any variants of the protein or antibody produced during manufacturing and/or storage. For example, during manufacturing or storage an antibody can be deamidated (e.g., at an asparagine or a glutamine residue) and/or have altered glycosylation and/or have a glutamine residue converted to pyroglutamine and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

SELECTED DEFINITIONS

VEGF-B is known to exist in two major isoforms, referred to as VEGF-$B_{186}$ and VEGF-$B_{167}$. For the purposes of nomenclature only and not limitation exemplary sequences of human VEGF-$B_{186}$ is set out in NCBI Reference Sequence: NP_003368.1, in NCBI protein accession numbers NP_003368, P49765 and AAL79001 and in SEQ ID NO: 1. In the context of the present disclosure, the sequence of VEGF-$B_{186}$ can lack the 21 amino acid N-terminal signal sequence (e.g., as set out at amino acids 1 to 21 of SEQ ID NO: 1. For the purposes of nomenclature only and not limitation exemplary sequences of human VEGF-$B_{167}$ is set out in NCBI Reference Sequence: NP_001230662.1, in NCBI protein accession numbers AAL79000 and AAB06274 and in SEQ ID NO: 2. In the context of the present disclosure, the sequence of VEGF-$B_{167}$ can lack the 21 amino acid N-terminal signal sequence (e.g., as set out at amino acids 1 to 21 of SEQ ID NO: 2. Additional sequence of VEGF-B can be determined using sequences provided herein and/or in publically available databases and/or determined using standard techniques (e.g., as described in Ausubel et al., (editors), Current Protocols in Molecular Biology. Greene Pub. Associates and Wiley-Interscience (1988, including all updates until present) or Sambrook et al., Molecular Cloning: A Laboratory Manual, Cold Spring Harbor Laboratory Press (1989)). Reference to human VEGF-B may be abbreviated to hVEGF-B. In one example, reference herein to VEGF-B is to VEGF-$B_{167}$ isoform.

Reference herein to VEGF-B also encompasses the VEGF-$B_{10-108}$ peptide as described in WO2006/012688.

The term "wound" will be taken to mean any injury in which a tissue of a subject is compromised (e.g., torn, pierced, cut, or otherwise broken).

As used herein, the term "dermal wound" shall be taken to mean a lesion to one or more layers of skin of a subject, e.g., wherein the lesion comprises one or more apoptotic dermal cells and/or one or more necrotic dermal cells. The term "dermal wound" shall be taken to include a wound that affects an epidermal layer of a subject and/or a dermal layer of a subject and/or a hypodermal layer of a subject.

The term "chronic wound" refers to a wound that does not heal in an orderly set of stages and in a predictable amount of time. Generally, wounds that do not heal within three months are considered chronic. Chronic wounds include, but are not limited to, e.g., arterial ulcers, diabetic ulcers, pressure ulcers, venous ulcers, etc. An acute wound can develop into a chronic wound.

The term "acute wound" or "normal wound" refers a wound that undergoes normal wound healing repair.

The term "progression of a wound" will be understood to mean a worsening of a wound, e.g., increasing in size and/or depth and/or progression to a more advanced stage and/or development of an infection.

The term "healing" in the context of the present disclosure is a promotion or acceleration of the time from when the compound is administered until significant or complete wound closure (full wound contraction).

The term "tissue" refers to a mass of cells in the human body which group together to form a specific function. Tissue includes, but is not limited to, skin, cartilage, and connective tissue.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein comprising an antibody variable region. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains, e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or λ light chain and a heavy chain from mammals is α, δ, ε, γ, or μ. Antibodies can be of any type (e.g., IgG, IgE, IgM, IgD. IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies, synhumanized antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid positions assigned to CDRs and FRs can be defined according to Kabat Sequences of Proteins of Immunological Interest, National Institutes of Health. Bethesda, Md., 1987 and 1991 or other numbering systems in the performance of this disclosure, e.g., the canonical numbering system of Chothia and Lesk J. Mol Biol. 196: 901-917, 1987; Chothia et al. Nature 342, 877-883, 1989; and/or Al-Lazikani et al., J Mol Biol 273: 927-948, 1997; the IMGT numbering system of Lefranc et al., Devel. And Compar. Immunol., 27: 55-77, 2003; or the AHO numbering system of Honnegher and Plükthun J. Mol. Biol., 309: 657-670, 2001.

"Framework regions" (FRs) are those variable domain residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to VEGF-B with materially greater affinity (e.g., 20 fold or 40 fold or 60 fold or 80 fold to 100 fold or 150 fold or 200 fold) than it does to other growth factor (e.g., VEGF-A) or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

As used herein, the term "neutralize" shall be taken to mean that a protein is capable of blocking, reducing or preventing VEGF-B-signaling in a cell through the VEGF-R1. Methods for determining neutralization are known in the art and/or described herein.

As used herein, the terms "preventing", "prevent" or "prevention" include administering a compound of the disclosure to thereby stop or hinder the development of at least one symptom of a condition.

As used herein, the terms "treating", "treat" or "treatment" include administering a protein described herein to thereby reduce or eliminate at least one symptom of a specified disease or condition or to slow progression of the disease or condition.

As used herein, the term "subject" shall be taken to mean any animal including humans, for example a mammal. Exemplary subjects include but are not limited to humans and non-human primates. For example, the subject is a human.

Treatment of Wounds

The present disclosure provides methods for accelerating and/or improving and/or enhancing healing of wounds, by administering a compound that inhibits VEGF-B signaling. For example, a method comprises administering the compound to a wound of a subject or systemically to a subject.

In one example, the subject suffers from a wound. The wound can be a chronic, acute or normal wound. In one example, the wound is chronic. In one example, the wound being treated is a stage 0A wound or a stage 1A wound or a Stage 2A wound or a Stage 3A wound as set out in Table 1. In one example, the wound being treated is a stage 0B wound or a stage 1B wound or a Stage 2B wound or a Stage 3B wound as set out in Table 1. In one example, the wound being treated is a stage 0C wound or a stage 1C wound or a Stage 2C wound or a Stage 3C wound as set out in Table 1. In one example, the wound being treated is a stage 0D wound or a stage 1D wound or a Stage 2D wound or a Stage 3D wound as set out in Table 1.

TABLE 1

Wound stages (as defined by the Texas Wound Classification System)

| Stage/ comorbidities | Wound grade/depth | | | |
| --- | --- | --- | --- | --- |
| | 0 | 1 | 2 | 3 |
| A | Pre- or post-ulcerative lesion completely epithelialized | Superficial ulcer not involving tendon, capsule or bone | Ulcer penetrating to tendon or capsule | Ulcer penetrating to bone or joint |
| B | As for 0, with infection | As for 1, with infection | As for 2, with infection | As for 3, with infection |
| C | As for 0, with ischemia | As for 1, with ischemia | As for 2, with ischemia | As for 3, with ischemia |
| D | As for 0, with infection and ischemia | As for 1, with infection and ischemia | As for 2, with infection and ischemia | As for 3, with infection and ischemia |

In one example, a subject suffers from a wound that is infected and/or ischemic.

In one example, the wound is a full-thickness wound.

In one example, the wound is a diabetic ulcer, e.g., a diabetic foot ulcer. Diabetic ulcers can be classified using the system set out in Table 1. In another example, the ulcer is classified according to the Wagner Ulcer Classification System as set out in Table 2.

TABLE 2

Wagner Ulcer Classification System

| Grade | Lesion |
| --- | --- |
| 1 | Superficial diabetic ulcer |
| 2 | Ulcer extension involving ligament, tendon, joint capsule or fascia with no abscess or osteomyelitis |
| 3 | Deep ulcer with abscess or osteomyelitis |
| 4 | Gangrene to portion of forefoot |
| 5 | Extensive gangrene of foot |

Examples of some of the risk factors for diabetic foot ulcers include peripheral neuropathy, which affects both motor and sensory functions of the foot, limited joint mobility, foot deformities, abnormal distribution of foot pressure, repetitive minor trauma, and impaired visual acuity. Peripheral sensory neuropathy is a primary factor. Approximately 45%-60% of all diabetic ulcerations are neuropathic, while up to 45% have both neuropathic and ischemic components. With an insensate foot, the patient is unable to perceive repetitive injury to the foot caused by, e.g., poor-fitting footwear during ambulation and activities of daily living. Neuropathy, combined with altered biomechanics of walking, leads to repetitive blunt trauma and distribution of abnormally high stress loads to vulnerable portions of the foot, resulting in callus formation and cutaneous erosion. Once an ulcer is formed, it is often slow to heal, can continue to enlarge, provides an opportunity for local or systemic infection, and requires comprehensive medical and surgical care to promote healing.

In one example, the wound is or has been present on the subject for at least about 2 weeks before administering a compound described herein. In one example, the wound is or has been present on the subject for at least about 4 weeks before administering a compound described herein. In one example, the wound is or has been present on the subject for at least about 6 weeks before administering a compound described herein.

Methods of the disclosure are also applicable to subjects who are undergoing or have undergone a treatment, wherein the treatment delays or provides ineffective wound healing. Treatments can include, but are not limited to, medications, radiation, treatments that results in suppressed immune systems, etc. In one example, a subject has a secondary condition, wherein the secondary conditions delays or provides ineffective wound healing. Secondary conditions, include, but are not limited to, e.g., diabetes, peripheral vascular disease, infection, autoimmune or collagen vascular disorders, disease states that result in suppressed immune systems, etc.

Quantitative analysis can be used to assess wound healing, e.g., determining the % reduction in the wound area, or complete wound closure (e.g., measured by skin closure without drainage or dressing requirements). Wound area is assessed before, during, and after treatment by methods known to those in the art. For example, assessment can be determined by, e.g., quantitative planimetry, photographs, physical examinations, etc. The wound area can be determined before, during and after treatment. In one example, the wound area can be estimated by measuring the length, L, of the wound, the longest edge-to-edge length in, e.g., cm, and the width, W, the longest edge-to-edge width perpendicular to L in, e.g., cm, and multiplying the L×W to get the estimated surface area (cm). The size of the wound for treatment can vary. In one example of the invention, the wound area before treatment is about 0.4 cm$^2$ or more, or about 1.0 cm$^2$ or more, or between about 0.4 cm$^2$ and about 10 cm$^2$, or between about 1 cm$^2$ and about 10 cm$^2$, or between about 1 cm$^2$ and about 7 cm$^2$, or between about 1 cm$^2$ and about 5 cm$^2$, or more than 4.0 cm$^2$. The area can be measured before or after debridement.

Acceleration of wound healing can be described by % acceleration of wound healing and/or a Hazard ratio. For example, the administration of a compound accelerates wound healing greater than 50%, or equal to or greater than 60%, equal to or greater than 70%, equal to or greater than 74%, equal to or greater than 75%, equal to or greater than 80%, equal to or greater than 85%, equal to or greater than 90%, equal to or greater than 95%, equal to or greater than 100%, equal to or greater than 110% or more, when compared to a control.

Methods of the disclosure encompass accelerating and/or improving and/or enhancing wound healing in a population of subjects. For example, a method comprises administering a compound to a subject of the population, wherein the administration of the compound results in greater than 10% (or greater than 12%, or 14%, or 15%, or 17%, or 20%, or 25%, or 30%, or 33%, or 35%, or 40%, or 45%, or 50% or more) improvement in wound healing in the population compared to a control.

Methods for reducing the recurrence of wounds (or ulcers) are also provided by the present disclosure. For example, a method comprises administering a compound to a subject such that the incidence of ulcer recurrence is reduced.

Methods for reducing the severity of a wound, e.g., in a subject at risk of developing a wound (e.g., a chronic wound) who is to undergo surgery (when a wound will be induced) are also provided.

In an alternative example, the disclosure provides a method for reducing scarring resulting from a wound in a subject, the method comprising administering to the subject a compound that inhibits VEGF-B signaling.

In a further alternative example, the disclosure provides a method for preventing formation of a wound (i.e., a new wound), the method comprising administering to the subject a compound that inhibits VEGF-B signaling.

VEGF-B Signaling Inhibitors

Proteins Comprising Antibody Variable Regions

An exemplary VEGF-B signaling inhibitor comprises an antibody variable region, e.g., is an antibody or an antibody fragment that binds to VEGF-B and neutralizes VEGF-B signaling.

In one example, the antibody variable region binds specifically to VEGF-B.

Suitable antibodies and proteins comprising variable regions thereof are known in the art.

For example, anti-VEGF-B antibodies and fragments thereof are described in WO2006/012688.

In one example, the anti-VEGF-B antibody or fragment thereof is an antibody that competitively inhibits the binding of 2H10 to VEGF-B or an antigen binding fragment thereof. In one example, the anti-VEGF-B antibody or fragment thereof is antibody 2H10 or a chimeric, CDR grafted or humanized version thereof or an antigen binding fragment thereof. In this regard, antibody 2H10 comprises a $V_H$ comprising a sequence set forth in SEQ ID NO: 3 and a $V_L$ comprising a sequence set forth in SEQ ID NO: 4. Exemplary chimeric and humanized versions of this antibody are described in WO2006/012688.

In one example, the anti-VEGF-B antibody or fragment thereof comprises a $V_H$ comprising a sequence set forth in SEQ ID NO: 5 and a $V_L$ comprising a sequence set forth in SEQ ID NO: 6.

In one example, the anti-VEGF-B antibody or fragment thereof is an antibody that competitively inhibits the binding of 4E12 to VEGF-B or an antigen binding fragment thereof. In one example, the anti-VEGF-B antibody or fragment thereof is antibody 4E12 or a chimeric, CDR grafted or humanized version thereof or an antigen binding fragment thereof. In this regard, antibody 4E12 comprises a $V_H$ comprising a sequence set forth in SEQ ID NO: 7 and a $V_L$ comprising a sequence set forth in SEQ ID NO: 8.

In one example, the compound is a protein comprising a humanized variable region of antibody 4E12. For example, the protein comprises a variable region comprising the complementarity determining regions (CDRs) of the $V_H$ and/or the $V_L$ of antibody 4E12. For example, the protein comprises:

(i) a $V_H$ comprising:
 (a) a CDR1 comprising a sequence set forth in amino acids 25-34 of SEQ ID NO: 7;
 (b) a CDR2 comprising a sequence set forth in amino acids 49-65 of SEQ ID NO: 7; and
 (c) a CDR3 comprising a sequence set forth in amino acids 98-105 of SEQ ID NO: 7; and/or
(ii) a $V_L$ comprising:
 (a) a CDR1 comprising a sequence set forth in amino acids 24-34 of SEQ ID NO: 8;
 (b) a CDR2 comprising a sequence set forth in amino acids 50-56 of SEQ ID NO: 8; and
 (c) a CDR3 comprising a sequence set forth in amino acids 89-97 of SEQ ID NO: 8.

In one example, the anti-VEGF-B antibody or fragment thereof is an antibody that competitively inhibits the binding of 2F5 to VEGF-B or an antigen binding fragment thereof. In one example, the anti-VEGF-B antibody or fragment thereof is antibody 2F5 or a chimeric, CDR grafted or humanized version thereof or an antigen binding fragment thereof. In this regard, antibody 2E5 comprises a $V_H$ comprising a sequence set forth in SEQ ID NO: 9 and a $V_L$ comprising a sequence set forth in SEQ ID NO: 10.

In one example, the compound is a protein comprising a humanized variable region of antibody 2F5. For example, the protein comprises a variable region comprising the complementarity determining regions (CDRs) of the $V_H$ and/or the $V_L$ of antibody 2F5. For example, the protein comprises:

(i) a $V_H$ comprising:
 (a) a CDR1 comprising a sequence set forth in amino acids 25-34 of SEQ ID NO: 9;
 (b) a CDR2 comprising a sequence set forth in amino acids 49-65 of SEQ ID NO: 9; and
 (c) a CDR3 comprising a sequence set forth in amino acids 98-107 of SEQ ID NO: 9; and/or
(ii) a $V_L$ comprising:
 (a) a CDR1 comprising a sequence set forth in amino acids 24-34 of SEQ ID NO: 10;
 (b) a CDR2 comprising a sequence set forth in amino acids 50-56 of SEQ ID NO: 10; and
 (c) a CDR3 comprising a sequence set forth in amino acids 89-96 of SEQ ID NO: 10.

In another example, an antibody or protein comprising a variable region thereof is produced using a standard method, e.g., as is known in the art or briefly described herein.

Immunization-Based Methods

To generate antibodies, VEGF-B or an epitope bearing fragment or portion thereof or a modified form thereof or nucleic acid encoding same (an "immunogen"), optionally formulated with any suitable or desired adjuvant and/or pharmaceutically acceptable carrier, is administered to a subject (for example, a non-human animal subject, such as, a mouse, a rat, a chicken etc.) in the form of an injectable composition. Exemplary non-human animals are mammals, such as murine animals (e.g., rats or mice). Injection may be intranasal, intramuscular, sub-cutaneous, intravenous, intradermal, intraperitoneal, or by other known route. Optionally, the immunogen is administered numerous times. Means for preparing and characterizing antibodies are known in the art (See, e.g., Antibodies: A Laboratory Manual, Cold Spring Harbor Laboratory, 1988). Methods for producing anti-VEGF-B antibodies in mice are described in WO2006/012688.

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. Generally, production of monoclonal antibodies involves, immunizing a subject (e.g., a rodent, e.g., mouse or rat) with the immunogen under conditions sufficient to stimulate antibody producing cells. In some examples, a mouse genetically-engineered to express human antibodies and not express murine antibodies proteins, is immunized to produce an antibody (e.g., as described in PCT/US2007/008231 and/or Lonberg et al., Nature 368 (1994): 856-859). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, Nature 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, Curr. Top. Microbiol. Immunol, 166, 91-96. 1990).

Library-Based Methods

The present disclosure also encompasses screening of libraries of antibodies or proteins comprising antigen binding domains thereof (e.g., comprising variable regions thereof) to identify a VEGF-B binding antibody or protein comprising a variable region thereof.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or U.S. Pat. No. 6,248,516.

The proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300,064; 5,885,793; 6,204,023; 6,291,158; or U.S. Pat. No. 6,248,516. Other phage display methods are known in the art and are contemplated by the present disclosure. Similarly, methods of cell display are contemplated by the disclosure. e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding domains displayed by the library with a target antigen (e.g., VEGF-B) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., J Immunol Methods. 354:85-90, 2010; or Jostock et al., J Immunol Methods, 289: 65-80, 2004. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001).

Deimmunized, Chimeric, Humanized, Synhumanized, Primatized and Human Proteins

The proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized protein" also encompasses a super-humanized protein. e.g., as described in U.S. Pat. No. 7,732,578.

The proteins of the present disclosure may be human proteins. The term "human protein" as used herein refers to proteins having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. Nos. 6,300,064 and/or 6,248,516.

The proteins of the present disclosure may be synhumanized proteins. The term "synhumanized protein" refers to a protein prepared by a method described in WO2007/019620. A synhumanized protein includes a variable region of an antibody, wherein the variable region comprises FRs from a New World primate antibody variable region and CDRs from a non-New World primate antibody variable region. For example, a synhumanized protein includes a variable region of an antibody, wherein the variable region comprises FRs from a New World primate antibody variable region and CDRs from a mouse or rat antibody.

The proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example a protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397).

The present disclosure also contemplates a deimmunized protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein.

Other Proteins Comprising Antibody Variable Regions

The present disclosure also contemplates other proteins comprising a variable region or antigen binding domain of an antibody, such as:
(i) a single-domain antibody, which is a single polypeptide chain comprising all or a portion of the $V_H$ or a $V_L$ of an antibody (see, e.g., U.S. Pat. No. 6,248,516);
(ii) diabodies, triabodies and tetrabodies, e.g., as described in U.S. Pat. No. 5,844,094 and/or US2008152586;
(iii) scFvs, e.g., as described in U.S. Pat. No. 5,260,203;
(iv) minibodies, e.g., as described in U.S. Pat. No. 5,837,821;
(v) "key and hole" bispecific proteins as described in U.S. Pat. No. 5,731,168;
(vi) heteroconjugate proteins, e.g., as described in U.S. Pat. No. 4,676,980;
(vii) heteroconjugate proteins produced using a chemical cross-linker, e.g., as described in U.S. Pat. No. 4,676,980;
(viii) Fab'-SH fragments, e.g., as described in Shalaby et al, J. Exp. Med., 175: 217-225, 1992; or
(ix) $Fab_3$ (e.g., as described in EP19930302894).

Constant Domain Fusions

The present disclosure encompasses a protein comprising a variable region of an antibody and a constant region or Fc or a domain thereof, e.g., $C_H2$ and/or $C_H3$ domain. Suitable constant regions and/or domains will be apparent to the skilled artisan and/or the sequences of such polypeptides are readily available from publicly available databases. Kabat et al also provide description of some suitable constant regions/domains.

Constant regions and/or domains thereof are useful for providing biological activities such as, dimerization, extended serum half-life e.g., by binding to FcRn (neonatal Fc Receptor), antigen dependent cell cytotoxicity (ADCC), complement dependent cytotoxicity (CDC, antigen dependent cell phagocytosis (ADCP).

The present disclosure also contemplates proteins comprising mutant constant regions or domains, e.g., as described in U.S. Pat. Nos. 7,217,797; 7,217,798; or US20090041770 (having increased half-life) or US2005037000 (increased ADCC).

Stabilized Proteins

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., Proc. Natl. Acad. USA, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional Protein-Based VEGF-B Signaling Inhibitors

Other proteins that may interfere with the productive interaction of VEGF-B with its receptor include mutant VEGF-B proteins.

In one example, the inhibitor is a soluble protein comprising one or more domains of a VEGF-R1 that bind to VEGF-B (and, e.g., do not substantially bind to VEGF-A). In one example, the soluble protein additionally comprises a constant region of an antibody, such as an IgG1 antibody. For example, the soluble protein additionally comprises a Fc region and, optionally a hinge region of an antibody. e.g., an IgG1 antibody.

In one example, the protein inhibitor is an antibody mimetic, e.g., a protein scaffold comprising variable regions that bind to a target protein in a manner analogous to an antibody. A description of exemplary antibody mimetics follows.

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies) in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678. WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Methods for Producing Proteins

Recombinant Expression

In the case of a recombinant protein, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce an antibody. Exemplary cells used for expressing a protein of the disclosure are CHO cells, myeloma cells or HEK cells. Molecular cloning techniques to achieve these ends are known in the art and described, for example in Ausubel et al., (editors). Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an antibody (e.g., derived from the information provided herein), an enhancer element, a promoter, and a transcription termination sequence. The skilled artisan will be aware of suitable sequences for expression of an antibody. Exemplary signal sequences include prokaryotic secretion signals (e.g., pelB, alkaline phosphatase, penicillinase, Ipp, or heat-stable enterotoxin II), yeast secretion signals (e.g., invertase leader, $\alpha$ factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-$\alpha$ promoter (EF1), small nuclear RNA promoters (U1a and U1b), $\alpha$-myosin heavy chain promoter. Simian virus 40 promoter (SV40), Rous sarcoma virus promoter (RSV), Adenovirus major late promoter, $\beta$-actin promoter; hybrid regulatory element comprising a CMV enhancer/$\beta$-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris*, *Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI. USA) amongst others.

The host cells used to produce the antibody may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Protein Purification

Following production/expression, a protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g. 95%, 98% or 99%) of the protein in the preparation is a protein of the disclosure.

Standard methods of peptide purification are employed to obtain an isolated protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition. Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a protein comprising a Fc region of an antibody, protein A or protein G or modified forms thereof can be used for affinity purification. Protein A is useful for isolating purified proteins comprising a human $\gamma 1$, $\gamma 2$, or $\gamma 4$ heavy chain Fc region. Protein G is recommended for all mouse Fc isotypes and for human $\gamma 3$.

Nucleic Acid-Based VEGF-B Signaling Inhibitors

In one example of the disclosure, therapeutic and/or prophylactic methods as described herein according to any example of the disclosure involve reducing expression of VEGF-B. For example, such a method involves administering a compound that reduces transcription and/or translation of the nucleic acid. In one example, the compound is a nucleic acid. e.g., an antisense polynucleotide, a ribozyme, a PNA, an interfering RNA, a siRNA or a microRNA.

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding VEGF-B, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding VEGF-B. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against VEGF-B are described, for example, in WO2003/105754.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNA-zyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding a VEGF-B. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The 30 degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search. Exemplary siRNA that reduce expression of VEGF-B are commercially available from Santa Cruz Biotechnology or Novus Biologicals.

Short hairpin RNA (shRNA) that reduce expression of VEGF-B are also known in the art and commercially available from Santa Cruz Biotechnology.

Screening Assays

Compounds that inhibit VEGF-B signaling can be identified using techniques known in the art, e.g., as described below. Similarly, amounts of VEGF-B signaling inhibitors suitable for use in a method described herein can be determined or estimated using techniques known in the art, e.g., as described below.

Neutralization Assays

For compounds that bind to VEGF-B and inhibit signaling, a neutralization assay can be used.

In one example, a neutralization assay involves contacting VEGF-B with a compound in the presence or absence of detectably labeled soluble VEGF-R1 or contacting detectably labeled VEGF-B with a compound in the presence or absence of a cell expressing VEGF-R1 or a soluble VEGF-R1. The level of VEGF-B bound to the VEGF-R1 is then assessed. A reduced level of bound VEGF-B in the presence of the compound compared to in the absence of the compound indicates the compound inhibits VEGF-B binding to VEGF-R1 and, as a consequence VEGF-B signaling.

Another neutralization assay is described in WO2006/012688 and involves contacting a fragment of VEGF-R1 comprising the second Ig-like domain immobilized on a solid support with a subsaturating concentration of recombinant VEGF-B pre-incubated with a compound. Following washing to remove unbound protein, the immobilized protein is contacted with anti-VEGF-B antibody and the amount of bound antibody (indicative of immobilized VEGF-B) determined. A compound that reduces the level of bound antibody compared to the level in the absence of the compound is considered an inhibitor of VEGF-B signaling.

In another example, a compound that inhibits VEGF-B signaling is identified using a cell dependent on VEGF-B signaling for proliferation, e.g., a BaF3 cell modified as described in WO2006/012688 to express a chimeric receptor incorporating the intracellular domain of the human erythropoietin receptor and the extracellular domain of VEGF-R1. Cells are cultured in the presence of VEGF-B and in the presence or absence of a compound. Cell proliferation is then assessed using standard methods, e.g., colony formation assays, thymidine incorporation or uptake of another suitable marker of cell proliferation (e.g., a MTS dye reduction assay). A compound that reduces the level of proliferation in the presence of VEGF-B is considered an inhibitor of VEGF-B signaling.

Compounds can also be assessed for their ability to bind to VEGF-B using standard methods. Methods for assessing binding to a protein are known in the art, e.g., as described in Scopes (In: Protein purification: principles and practice, Third Edition, Springer Verlag, 1994). Such a method generally involves labeling the compound and contacting it with immobilized VEGF-B. Following washing to remove non-specific bound compound, the amount of label and, as a consequence, bound compound is detected. Of course, the compound can be immobilized and the VEGF-B labeled. Panning-type assays can also be used. Alternatively, or additionally, surface plasmon resonance assays can be used.

Expression Assays

A compound that reduces or prevents expression of VEGF-B is identified by contacting a cell with the compound and determining the level of expression of the VEGF-B. Suitable methods for determining gene expression at the nucleic acid level are known in the art and include, for example, quantitative polymerase chain reaction (qPCR) or microarray assays. Suitable methods for determining expression at the protein level are also known in the art and include, for example, enzyme-linked immunosorbent assay (ELISA), fluorescence linked immunosorbent assay (FLISA), immunofluorescence or Western blotting.

In Vitro Assays

Numerous in vitro assays have been described for assessing wound healing, including scrape or scratch assays in which a culture of endothelial cells or fibroblasts is scraped to produce a cell free area and the rate of closure of this cell free area is assessed in the presence or absence of a compound.

Other assays include the chick chorioallantoic membrane (CAM) model.

In Vivo Assays

There are numerous in vivo assays for assessing wound healing. For example, the present inventors have made use of a model in which diabetic animals are wounded (e.g., full-thickness wounds are produced) and the rate and/or amount of wound closure assessed over time in the presence or absence of a test compound.

Other models of chronic wound include, for example, the rabbit ear "ulcer" model, skin flap models, pressure ulcer models (e.g., by applying pressure to the leg of a greyhound using a cast) or subcutaneous Adriamycin administration.

Models of acute wounding include, for example, incisional models, excisional models and burn models.

Wounds can be produced in animals suffering from other defects, e.g., metabolic defects (e.g., as described herein or by administration of streptozotocin).

Various models of wounds are described, for example, in Demling et al., WOUNDS. 13(1 Suppl A):5-14, 2001 and in the FDA Guidelines for Chronic Cutaneous Ulcer and Burn Wounds.

Pharmaceutical Compositions and Methods of Treatment

A compound that inhibits VEGF-B signaling (syn. active ingredient) is useful for parenteral, topical, oral, or local administration, aerosol administration, or transdermal administration, for prophylactic or for therapeutic treatment. In one example, the compound is administered parenterally, such as subcutaneously or intravenously.

Formulation of a compound to be administered will vary according to the route of administration and formulation (e.g., solution, emulsion, capsule) selected. An appropriate pharmaceutical composition comprising compound to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The compound can be lyophilized for storage and reconstituted in a suitable carrier prior to use according to art-known lyophilization and reconstitution techniques.

In one example, the present disclosure provides a topical formulation comprising compound of the disclosure. In one example, the compound is formulated with a carrier suitable for topical formulation. Suitable carriers include a compound or mixture thereof that is suitable for application to one or more dermal layers not necessarily to the external layer of skin, and which may be suitable for use in other contexts. A carrier and excipient useful in the topical composition of the present disclosure will generally not inhibit to any significant degree a relevant biological activity of the active compound e.g., the carrier or excipient will not significantly inhibit the inhibitory activity of the active compound with respect to VEGF-B signaling. For example, the carrier or excipient provides a buffering activity to maintain the compound at a suitable pH to thereby exert its biological activity, e.g., the carrier or excipient is phosphate buffered saline. Alternatively, or in addition, the carrier or excipient comprises a compound that enhances uptake of the inhibitor and/or enhances transdermal delivery of the inhibitor. For example, the carrier or excipient comprises a skin penetration enhancer, such as, for example, dipropylene glycol and/or oleyl alcohol. Alternatively, or in addition, a carrier or excipient comprises a liposome to facilitate cellular uptake.

Alternatively, or in addition, the carrier or excipient comprises a compound that enhances the activity of a compound and/or reduces inhibition of the compound, e.g., a protease inhibitor and/or a DNase inhibitor and/or a RNase inhibitor to thereby enhance the stability of the inhibitor.

The optimum concentration of the active ingredient(s) in the chosen medium can be determined empirically, according to procedures known to the skilled artisan, and will depend on the ultimate pharmaceutical formulation desired.

The dosage ranges for the administration of the compound of the disclosure are those large enough to produce the desired effect. For example, the composition comprises a therapeutically or prophylactically effective amount of the compound.

As used herein, the term "effective amount" shall be taken to mean a sufficient quantity of the compound to inhibit/reduce/prevent signaling of VEGF-B in a subject. The skilled artisan will be aware that such an amount will vary depending on, for example, the compound and/or the particular subject and/or the type and/or the severity of a wound being treated. Accordingly, this term is not to be construed to limit the disclosure to a specific quantity, e.g., weight or number of compounds.

As used herein, the term "therapeutically effective amount" shall be taken to mean a sufficient quantity of compound to enhance or induce wound healing.

As used herein, the term "prophylactically effective amount" shall be taken to mean a sufficient quantity of compound to prevent or inhibit or delay progression of a wound.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, the compound is administered at an initial (or loading) dose which is higher than subsequent (maintenance doses). For example, the compound is administered at an initial dose of between about 1 mg/kg to about 30 mg/kg. The compound is then administered at a maintenance dose of between about 0.0001 mg/kg to about 1 mg/kg. The maintenance doses may be administered every 7-35 days, such as, every 14 or 21 or 28 days.

In some examples, a dose escalation regime is used, in which a compound is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

A subject may be retreated with the compound, by being given more than one exposure or set of doses, such as at least about two exposures of the compound, for example, from about 2 to 60 exposures, and more particularly about 2 to 40 exposures, most particularly, about 2 to 20 exposures.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

A method of the present disclosure may also include co-administration of the at least one compound according to the disclosure together with the administration of another therapeutically effective agent for the prevention or treatment of a wound and/or diabetes.

In one example, the compound(s) of the disclosure is used in combination with at least one additional known compound which is currently being used or is in development for preventing or treating diabetes. Examples of such known compounds include but are not limited to common anti-diabetic drugs such as sulphonylureas (e.g. glicazide, glipizide), metformin, glitazones (e.g. rosiglitazone, pioglitazone), prandial glucose releasing agents (e.g. repaglinide, nateglinide), acarbose and insulin (including all naturally-occurring, synthetic and modified forms of insulin, such as insulin of human, bovine or porcine origin; insulin suspended in, for example, isophane or zinc and derivatives such as insulin glulisine, insulin lispro, insulin lispro protamine, insulin glargine, insulin detemir or insulin aspart).

In one example, a compound of the disclosure is administered with a compound known to be useful for treating a wound. For example, the compound is administered in combination with an anti-infective (e.g., an antibiotic or an antifungal), VEGF-A, IGF-1, IGF-2, PDGF, TGF-β, EGF or a stem cell (e.g., a mesenchymal stem or progenitor cell or an endothelial stem cell).

In one example, a compound of the disclosure is administered with another treatment for a wound, for example a dressing and/or a graft and/or negative pressure.

Additional examples of agents that can be co-administered with the compound(s) according to the disclosure are corticosteroids and immunosuppressive medications.

As will be apparent from the foregoing, the present disclosure provides methods of concomitant therapeutic treatment of a subject, comprising administering to a subject in need thereof an effective amount of a first compound and a second compound, wherein said agent is a compound of the disclosure (i.e., an inhibitor of VEGF-B signaling), and the second agent is for the prevention or treatment of a wound or diabetes.

As used herein, the term "concomitant" as in the phrase "concomitant therapeutic treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

In one example, the disclosure also provides a method for treating or preventing a wound in a subject, the method comprising administering to the subject a first pharmaceutical composition comprising at least one compound of the disclosure and a second pharmaceutical composition comprising one or more additional compounds.

In one example, a method of the disclosure comprises administering an inhibitor of VEGF-B signaling to a subject suffering from a wound (e.g., a diabetic ulcer) and receiving another treatment (e.g., for diabetes).

Kits and Other Compositions of Matter

Another example of the disclosure provides kits containing compounds useful for the treatment of a wound as described above.

In one example, the kit comprises (a) a container comprising a compound that inhibits VEGF-B signaling as described herein, optionally in a pharmaceutically acceptable carrier or diluent; and (b) a package insert with instructions for treating a wound in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the a wound and may have a sterile access port (for example, the container may be an intravenous solution bag or a vial having a stopper pierceable by a hypodermic injection needle). At least one active agent in the composition is the compound that inhibits VEGF-B signaling. The label or package insert indicates that the composition is used for treating a subject eligible for treatment. e.g., one having or predisposed to a wound, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprises a second medicament, wherein the compound that inhibits VEGF-B signaling is a first medicament, and which article further comprises instructions on the package insert for treating the subject with the second medicament, in an effective amount or another treatment for a wound. The second medicament may be any of those set forth above.

The present disclosure also provides a dressing for a wound impregnated or having immobilized therein (e.g., reversibly immobilized therein) a compound as disclosed herein. Exemplary dressings include bandages, for example, a fabric bandage or a plastic bandage or a gauze bandage or a gauze dressing or a trauma dressing. Alternatively, or in addition, the dressing comprises a scaffold, e.g., a biodegradable scaffold. For example, the scaffold comprises collagen and/or poly(lactic) acid and/or poly(glycolic) acid and/or fibrin. Such a scaffold may be porous or non-porous or a mixture thereof. An advantage of such scaffolds is that they adapt to the shape of a wound and deliver a therapeutic compound to the site of wounding. Moreover, as the wound heals, the scaffold breaks down, thereby reducing biological waste.

The present disclosure includes the following non-limiting Examples.

Example 1: A Neutralizing Anti-VEGF-B Antibody Treats Wounds in Diabetic Mice

Antibody-Mediated Inhibition of VEGF-B Moderately Influences Blood Glucose Levels in Diabetic db/db//BKS Mice In-house bred male C57BKS/Leprdb (db/db/BKS) mice were purchased from Jackson Laboratory. Mice were housed in one-mouse per cage prior wounding and during the experiment. The animal facility has a 12-hour dark/light cycle with food and water available ad libitum. Enrichment included rat tunnels and nesting material to reduce stress. db/db/BKS male mice (8 weeks) were pre-treated 2 times/week (i.p.) for 4 weeks prior to wounding, with 400 µg VEGF-B-antibody (2H10) or an isotype matched control antibody (BM4). The same treatment regime continued after wounding until sacrificing the animals. Body weight and blood glucose were monitored prior to and during the experiment. Blood glucose levels were analyzed from the tail using a blood glucose meter (Countour stick, Bayer) and weight was measured with a laboratory scale.

Figure 1B:
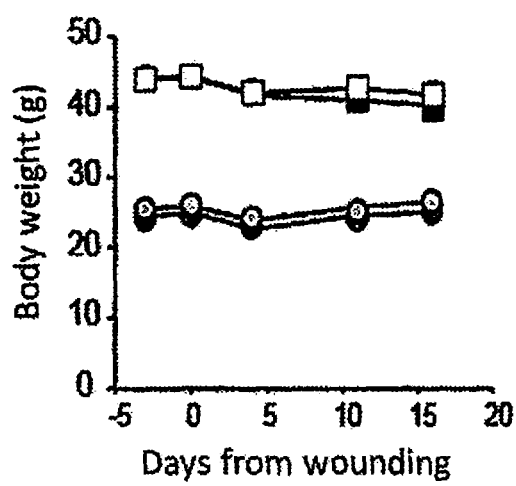

As shown in FIGS. 1A and 1B, in this experiment Anti-VEGF-B treatment did not alter blood glucose levels or weight gain in severe diabetic db/db BKS mice or in non-diabetic db/+ BKS mice.

Pharmacological Inhibition of VEGF-B Using 2H10 Enhances Wound Closure in a Severely Diabetic Mouse Model.

After reaching non-fasting blood glucose levels above 15 mM, 2H10 or BM4 (control) treated db/db or db/+ were kept for an additional two weeks before wounding. This was done in order to obtain severely diabetic animals at the time of wounding. Wounding was performed under general anaesthesia by isoflurane inhalation. Hair behind the neck was removed with an electric hair clipper and by application of a depilatory cream (Veet). The skin was disinfected with 70% ethanol, after which two paired circular full-thickness wounds that penetrate the skin and panniculus carnosus were made using a 6 mm biopsy punch. During the first two days after wounding, mice were given subcutaneous analgesic injections of 0.05-0.1 mg/kg buprenorphine twice per day. Wound size and the healing progression were traced with digital photography directly after wounding and then every other day during the experiment. The wound area was measured twice for every wound by using Image J software. The distance between the camera and the wound was corrected by relating the size of the wound to a reference object included in every image. A single wound (two per animal) was treated as a single experimental data point.

Figure 2:
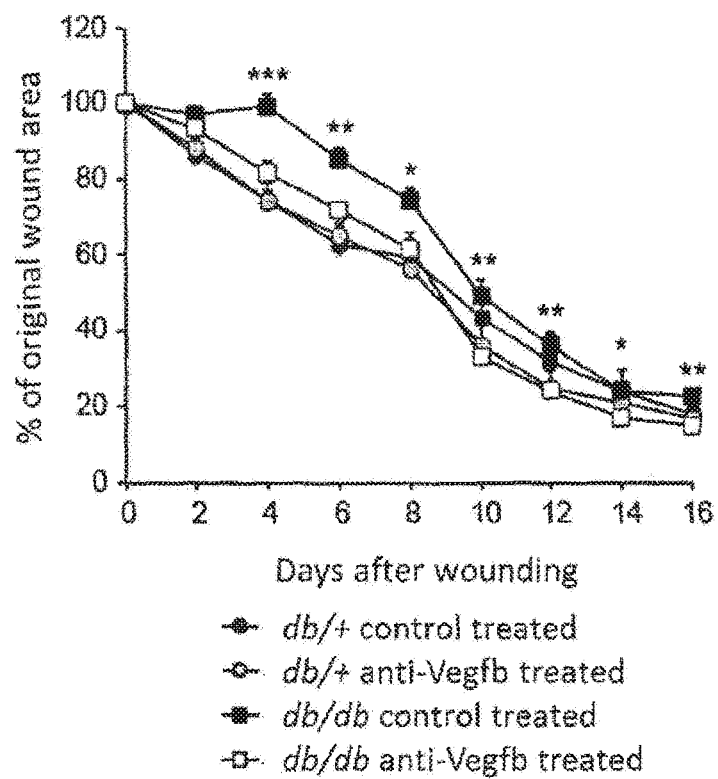
FIG. 2 is a graphical representation showing pharmacological inhibition of VEGF-B using 2H10 enhances wound closure in a severely diabetic mouse model. Improved wound closure is detected upon pharmacological VEGF-B inhibition in diabetic db/db BKS animals. No differences in wound closure are found in non-diabetic db/+ BKS mice upon VEGF-B inhibition (n=8-14/group). Values are means±s.e.m. *P<0.05, P<0.01, *P<0.001 compared to db/db control treated mice.

As shown in FIG. 2 wound closure is significantly enhanced in a diabetic mouse model (db/db BKS) when treated with an anti-VRGF-B antibody.

Figure 3A:
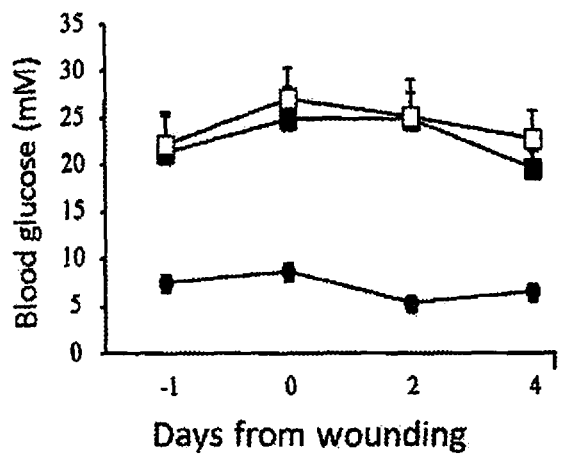
FIGS. 3A and 3B include a series of graphical representations showing anti-VEGF-B treatment, using 2H10 accelerates wound healing, despite no differences in blood glucose levels, in short time periods. Analysis of db/db animals treated with 2H10 or control antibody, and db/+ animals.
Figure 3B:
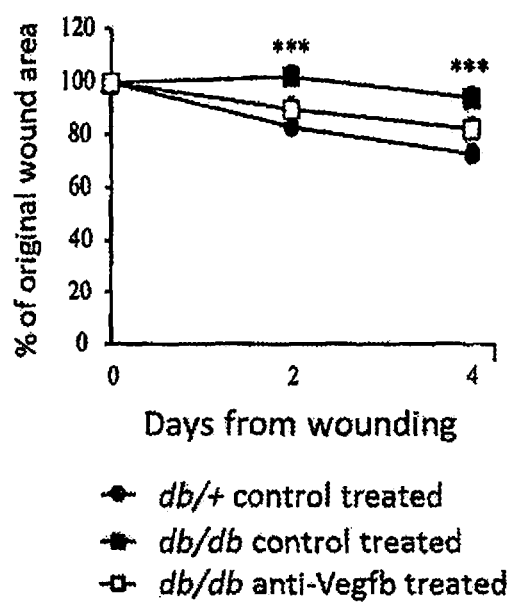

Anti-VEGF-B treatment increased the rate of wound closure and healing in a diabetic mouse model. The most prominent effect of anti-VEGF-B treatment was detected in the early phase of wound closure (day 4 and 6). This is further shown in FIGS. 3A and 3B, in which anti-VEGF-B treatment accelerates wound healing during the first four days, despite no differences in blood glucose levels.

The data presented herein suggest that the hyperglycaemia in diabetes per se is not the main reason for the impaired wound healing process.

Anti-VEGF-B Treatment Using 2H10 Decreases Expression of Genes Up-Regulated in Wound Healing Male db/db and db/+ mice (treated as described above and sacrificed at day 16) were used for expression analysis. Wounds were dissected and flash frozen on dry ice. Total RNA was extracted and purified from wounds using the RNeasy Mini kit (Qiagen) according to the manufacturer's instructions. First strand cDNA was synthesized from 0.5-1 µg total RNA using iScript cDNA Synthesis Kit (Bio-Rad). Real-Time quantitative PCR was performed using KAPA SYBR FAST qPCR Kit Master Mix (2×) Universal (KAPA Biosystems) in Rotor-Gene Q (Qiagen) Real-Time PCR thermal cycler according to the manufacturers' instructions. Expression levels were normalized to the expression of L19.

Figure 4:
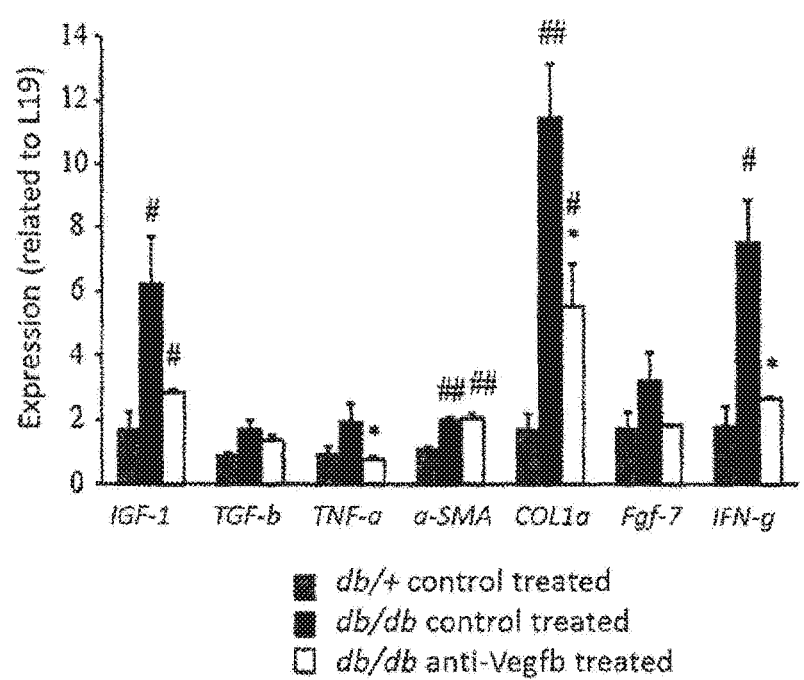
FIG. 4 is a graphical representation showing anti-VEGF-B treatment, using 2H10, reduces expression of several genes that are up-regulated during diabetic wounding. End-point IGF-1, TGF-b, TNF-α, α-SMA, COL1α, Fgf-7 and IFN-γ expression levels were measured in db/db mice treated with 2H10 or control antibody, and in control treated db/+ mice (n=8-14/group). Values are means±s.e.m. * P<0.05, compared with db/db animals control treated, # P<0.05, ## P<0.01, compared to control treated db/+ mice animals. IGF-1; Insulin-like growth factor 1, TGF-b; transforming growth factor beta, TNF-α; Tumor necrosis factor, α-SMA; alpha smooth muscle actin, COL1a; alpha-1 type I collagen. Fgf-7; fibroblast growth factor 7.

As shown in FIG. 4, anti-VEGF-B treatment in db/db mice reduces expression of several genes that are up-regulated during diabetic wounding.

Anti-VEGF-B Treatment Using 2H10 Affects Blood Vessel Morphology but does not Promote Cell Proliferation Male db/db mice (treated as described above and sacrificed at day 16) were used for immunological analyses. Wounds were dissected and fixed in paraformaldehyde in +4° C. for 24 hours, hydrated in 70% ethanol, embedded in paraffin and sectioned in 3 µm thick cross sections. Antigen retrieval was performed using antigen retrieval solution pH6 (DAKO) and by heating sections to +98° C. for 10 minutes. Sections were incubated at +4° C. for 12 hours with appropriate primary antibodies (Brdu, CD45. CIV and CD31, diluted to 1-5 µg/mL). Matching fluorescently labelled secondary antibodies (Invitrogen, Alexa fluor, diluted 1:1000) were applied and sections incubated for 1 hr at room temperature (RT) after which they were prepared for microscopy. Sections were photographed with an AxioVision microscope (Carl Zeiss) at 20× magnification. Sections were then evaluated and quantified using AxioVision Run wizard program (pixels2). BrdU staining intensity was quantified in relation to counterstaining intensity of DAPI and all other staining was quantified for total pixel area.

Figure 5A:
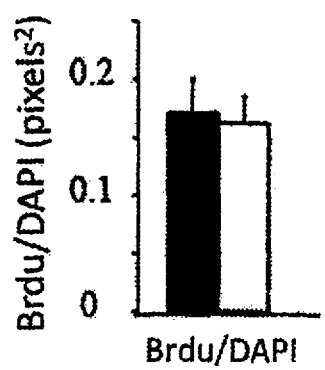
FIGS. 5A and 5B include a series of graphical representations showing VEGF-B inhibition in db/db mice affects blood vessel morphology but does not promote cell proliferation.
Figure 5B:
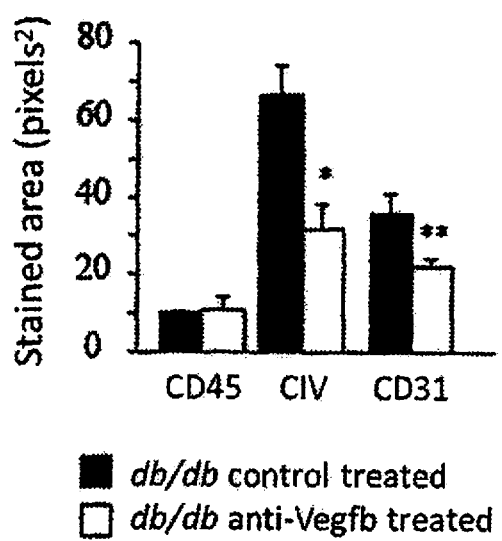

As shown in FIGS. 5A and 5B, anti-VEGF-B treatment promotes the maturation of blood vessels during diabetic wound healing.

VEGF-B Signalling Pathway is Up-Regulated in Diabetic Wounds

Control antibody (BM4) treated db/db or db/+ were wounded essentially as described above and sacrificed at day 16 after wounding. Wounds were taken with a 6 mm biopsy punch for expression and histological analyses. Tissues where frozen in liquid nitrogen and kept at −80° C. until further processing. RNA was isolated with TRIzol reagent (Invitrogen) and QIAGEN RNeasy (Qiagen) according to the manufacturer's instructions. Total RNA (500 ng) was reverse transcribed according to the manufacturer's instructions (iScript cDNA synthesis kit, Bio-Rad). qPCR was performed using Platinum SYBR green SuperMix (Invitrogen) and 25 ng cDNA per reaction. Expression levels were normalized to the expression of TUBB5 (tubulin, beta 5 class 1).

Figure 6:
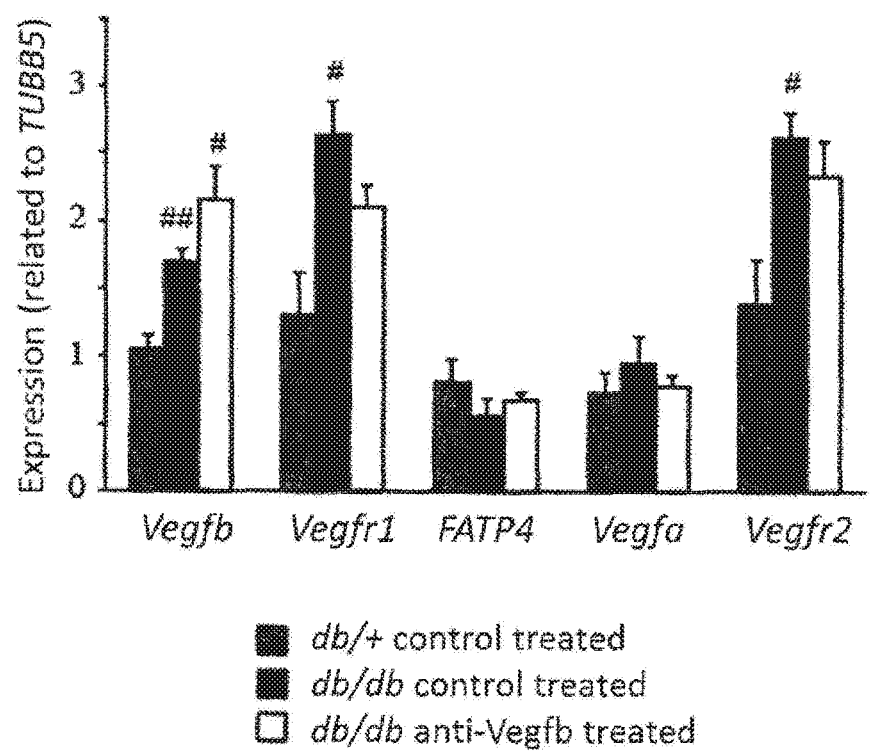
FIG. 6 is a graphical representation showing VEGF-B signaling pathway is up-regulated in diabetic wounds. Endpoint Vegfb, Vegfr1, Fatp4, Vegfa and Vegfr2 expression levels were measured in tissue from wounds from diabetic db/db mice and non-diabetic db/+ mice. Expression levels are normalized to TUBB5. Values are means±s.e.m. #P<0.05, ##P<0.01, db/db control treated compared to db/+ control treated, n=3-5. Vegfb; vascular endothelial growth factor B; Vegfr1; vascular endothelial growth factor receptor 1, Fatp4; fatty acid transporter 4, Vegfa; vascular endothelial growth factor A; Vegfr2; vascular endothelial growth factor receptor 2.

As shown in FIG. 6, expression of Vegfb and the VEGF-B binding receptor, Vegfr1 are increased with diabetes and obesity in wounds. These data indicate that the VEGF-B signaling pathway is a suitable target for treating diabetic wounding.

Anti-VEGF-B Treatment Using 2H10 Decreases Lipid Accumulation in Skin in db/db Mice Male db/db, and db/+ mice (treated as described above) were used for Oil red O (ORO) analysis. Wounds were dissected and flash frozen on dry ice and embedded in Tissue-Tek® (Sakura) directly on the mold of the cryostat. Cryosections (12 μm) were immersed 12 min in oil red O working solution (2.5 g oil red O (Sigma-Aldrich), dissolved in 400 ml 99% isopropanol, further diluted 6:10 in $H_2O$, filtered through a 22 μm filter (Corning)) and rinsed 20 min under running tap water before they were mounted. Stained sections were examined with bright field microscopy (Axio Vision microscope. Carl Zeiss) at 40× magnification and a minimum of 4 frames per animal were captured. Images were captured from the central area of the wound. For quantification of lipid droplets, the amount of red pixels in each frame was quantified using Axio Vision Run wizard program for total ORO staining (pixel, a.u).

Figure 7:
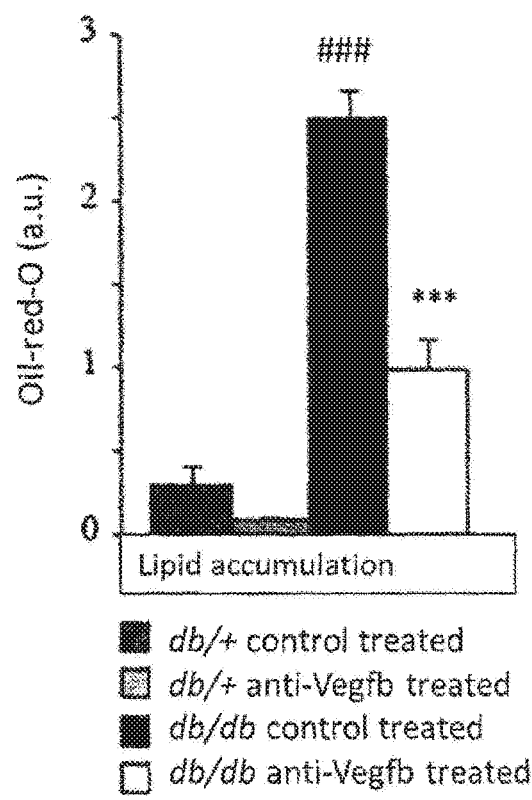
FIG. 7 is a graphical representation showing anti-VEGF-B treatment using 2H10 decreases lipid accumulation in skin in db/db mice. The depicted graph shows quantification of Oil red O staining in db/db and db/+ treated with control or 2H10 antibody. Values are means±s.e.m. ***P<0.001 db/db control treated compared to db/db 2H10 treated mice. ###P<0.001 Db/+ animals compared to db/db control treated mice.

As shown in FIG. 7, anti-VEGF-B treatment using 2H10 reduces lipid accumulation in skin after wounding in male db/db mice.

The invention claimed is:

1. A method for treating a dermal wound in a diabetic subject or for enhancing or inducing dermal wound healing in a diabetic subject suffering from a dermal wound or for reducing or preventing progression of a dermal wound in a diabetic subject, the method comprising administering to the subject a compound that inhibits VEGF-B signaling, wherein the compound that inhibits VEGF-B signaling is an antibody or antigen binding fragment thereof that binds or specifically binds to VEGF-B and comprises complementarity determining regions (CDRs) of a heavy chain variable region ($V_H$) comprising a sequence set forth in SEQ ID NO: 3, and CDRs of a light chain variable region ($V_L$) comprising a sequence set forth in SEQ ID NO: 4.

2. The method of claim 1, wherein the wound is acute or normal.

3. The method of claim 1, wherein the wound is chronic.

4. The method of claim 1, wherein the subject suffers from obesity.

5. The method of claim 1, wherein the antibody or antigen binding fragment thereof is administered in an amount effective to have one or more of the following effects:

(a) enhance the rate of wound closure compared to the rate in a subject suffering from diabetes and a wound to whom the antibody or antigen binding fragment thereof has not been administered; and/or (b) enhance the amount of wound closure at a specific point in time compared to the rate in a subject suffering from diabetes and a wound to whom the antibody or antigen binding fragment thereof has not been administered; and/or (c) enhance maturation of blood vessels in a subject compared to in a subject suffering from diabetes and a wound to whom the antibody or antigen binding fragment thereof has not been administered.

6. The method of claim 1, wherein the compound that inhibits VEGF-B signaling comprises an Fv.

7. The method of claim 6, wherein, the compound that inhibits VEGF-B signaling is selected from the group consisting of:

(i) a single chain Fv fragment (scFv);
(ii) a dimeric scFv (di-scFv);
(iii) a diabody;
(iv) a triabody;
(v) a tetrabody;
(vi) a Fab;
(vii) a F(ab')$_2$;
(viii) a Fv;
(ix) one of (i) to (viii) linked to a constant region of an antibody, Fc or a heavy chain constant domain ($C_H$)2 and/or $C_H$3; and
(x) an antibody.

8. The method of claim 7, wherein the antibody:
(i) comprises a humanized variable region of a $V_H$ comprising a sequence set forth in SEQ ID NO: 3 and a $V_L$ comprising a sequence set forth in SEQ ID NO: 4; or
(ii) comprises a $V_H$ comprising a sequence set forth in SEQ ID NO: 5 and a $V_L$ comprising a sequence set forth in SEQ ID NO: 6.

9. A method of treating a dermal wound in a diabetic subject or for enhancing or inducing dermal wound healing in a diabetic subject suffering from a dermal wound or for reducing or preventing progression of a dermal wound in a diabetic subject, the method comprising administering to the subject an antibody or antigen binding fragment thereof which comprises:
(i) a $V_H$ comprising
(a) a CDR1 comprising a sequence set forth in amino acids 25-34 of SEQ ID NO: 3;
(b) a CDR2 comprising a sequence set forth in amino acids 49-65 of SEQ ID NO: 3; and
(c) a CDR3 comprising a sequence set forth in amino acids 98-108 of SEQ ID NO: 3; and
(ii) a $V_L$ comprising:
(a) a CDR1 comprising a sequence set forth in amino acids 23-33 of SEQ ID NO: 4;
(b) a CDR2 comprising a sequence set forth in amino acids 49-55 of SEQ ID NO: 4; and
(c) a CDR3 comprising a sequence set forth in amino acids 88-96 of SEQ ID NO: 4.

10. The method of claim 9, wherein the antibody or antigen binding fragment thereof comprises a $V_H$ comprising a sequence set forth in SEQ ID NO: 5 and a $V_L$ comprising a sequence set forth in SEQ ID NO: 6.

* * * * *